United States Patent
Smith et al.

(10) Patent No.: US 9,358,365 B2
(45) Date of Patent: Jun. 7, 2016

(54) PRECISION ELECTRODE MOVEMENT CONTROL FOR RENAL NERVE ABLATION

(75) Inventors: Scott Smith, Chaska, MN (US); Leonard B. Richardson, Minneapolis, MN (US); Mark L. Jenson, Greenfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1306 days.

(21) Appl. No.: 13/194,920

(22) Filed: Jul. 30, 2011

(65) Prior Publication Data

US 2012/0029513 A1 Feb. 2, 2012

Related U.S. Application Data

(60) Provisional application No. 61/369,463, filed on Jul. 30, 2010.

(51) Int. Cl.
*A61B 18/14* (2006.01)
*A61M 25/01* (2006.01)
(Continued)

(52) U.S. Cl.
CPC ....... *A61M 25/0113* (2013.01); *A61M 25/0127* (2013.01); *A61M 25/0138* (2013.01); *A61B 18/1492* (2013.01); *A61B 18/1815* (2013.01);
(Continued)

(58) Field of Classification Search
CPC ........... A61B 18/1492; A61B 1/00073; A61B 1/00135; A61B 1/00154; A61M 25/0113; A61M 25/0138; A61M 25/0054; A61M 25/0147

USPC .......................................................... 606/41
See application file for complete search history.

(56) References Cited

U.S. PATENT DOCUMENTS

| 164,184 A | 6/1875 | Kiddee |
| 1,167,014 A | 1/1916 | O'Brien |

(Continued)

FOREIGN PATENT DOCUMENTS

| DE | 10038737 A1 | 2/2002 |
| EP | 1053720 A1 | 11/2000 |

(Continued)

OTHER PUBLICATIONS

U.S. Appl. No. 12/980,952, filed Dec. 29, 2010, Rizq et al.
(Continued)

*Primary Examiner* — Joseph Stoklosa
*Assistant Examiner* — Eunhwa Kim
(74) *Attorney, Agent, or Firm* — Kacvinsky Daisak Bluni PLLC

(57) ABSTRACT

A catheter is configured to access a renal artery. A lumen of the catheter's shaft is dimensioned to receive a flexible actuation member which extends between the shaft's proximal and distal ends. The actuation member is moveable within the lumen and subject to elastic deformation, friction, and/or whip along its length. A flexible support member is coupled to a distal end of the actuation member and extendible beyond a distal tip of the shaft. An RF ablation electrode at a distal end of the support member is configured to ablated perivascular renal nerve tissue. A position converter at the distal end of the shaft is configured to convert movement of the actuation member into one or both of controlled rotational and axial movement of the support member and electrode to one of a multiplicity of stable circumferential positions substantially free of elastic deformation, friction, and/or whip impacting actuation member movement.

18 Claims, 15 Drawing Sheets

(51) Int. Cl.
  *A61B 18/18* (2006.01)
  *A61B 18/20* (2006.01)
  *A61B 19/00* (2006.01)
  *A61B 18/00* (2006.01)
  *A61M 25/00* (2006.01)

(52) U.S. Cl.
  CPC .............. *A61B 18/20* (2013.01); *A61B 19/54* (2013.01); *A61B 2018/00011* (2013.01); *A61B 2018/00434* (2013.01); *A61B 2018/00589* (2013.01); *A61B 2018/00791* (2013.01); *A61B 2018/00875* (2013.01); *A61M 25/0054* (2013.01); *A61M 25/0147* (2013.01)

(56) References Cited

U.S. PATENT DOCUMENTS

| | | | |
|---|---|---|---|
| 2,505,358 A | | 4/1950 | Gusberg et al. |
| 2,701,559 A | | 2/1955 | Cooper |
| 3,108,593 A | | 10/1963 | Glassman |
| 3,108,594 A | | 10/1963 | Glassman |
| 3,540,431 A | | 11/1970 | Mobin |
| 3,847,001 A | * | 11/1974 | Thamasett ........................ 72/96 |
| 3,952,747 A | | 4/1976 | Kimmell |
| 3,996,938 A | | 12/1976 | Clark, III |
| 4,046,150 A | | 9/1977 | Schwartz et al. |
| 4,290,427 A | | 9/1981 | Chin |
| 4,402,686 A | | 9/1983 | Medel |
| 4,483,341 A | | 11/1984 | Witteles et al. |
| 4,574,804 A | | 3/1986 | Kurwa |
| 4,587,975 A | | 5/1986 | Salo et al. |
| 4,649,936 A | | 3/1987 | Ungar et al. |
| 4,682,596 A | | 7/1987 | Bales et al. |
| 4,709,698 A | | 12/1987 | Johnston et al. |
| 4,765,331 A | | 8/1988 | Petruzzi et al. |
| 4,770,653 A | | 9/1988 | Shturman |
| 4,784,132 A | | 11/1988 | Fox et al. |
| 4,784,162 A | | 11/1988 | Ricks et al. |
| 4,785,806 A | | 11/1988 | Deckelbaum et al. |
| 4,788,975 A | | 12/1988 | Shturman et al. |
| 4,790,310 A | | 12/1988 | Ginsburg et al. |
| 4,799,479 A | | 1/1989 | Spears |
| 4,823,791 A | | 4/1989 | D'Amelio et al. |
| 4,830,003 A | | 5/1989 | Wolff et al. |
| 4,849,484 A | | 7/1989 | Heard |
| 4,862,886 A | | 9/1989 | Clarke et al. |
| 4,887,605 A | | 12/1989 | Angelsen et al. |
| 4,920,979 A | | 5/1990 | Bullara et al. |
| 4,938,766 A | | 7/1990 | Jarvik |
| 4,955,377 A | | 9/1990 | Lennox et al. |
| 4,976,711 A | | 12/1990 | Parins et al. |
| 5,034,010 A | | 7/1991 | Kittrell et al. |
| 5,052,402 A | | 10/1991 | Bencini et al. |
| 5,053,033 A | | 10/1991 | Clarke et al. |
| 5,071,424 A | | 12/1991 | Reger et al. |
| 5,074,871 A | | 12/1991 | Groshong et al. |
| 5,098,429 A | | 3/1992 | Sterzer et al. |
| 5,098,431 A | | 3/1992 | Rydell |
| 5,109,859 A | | 5/1992 | Jenkins |
| 5,125,928 A | | 6/1992 | Parins et al. |
| 5,129,396 A | | 7/1992 | Rosen et al. |
| 5,139,496 A | | 8/1992 | Hed |
| 5,143,836 A | | 9/1992 | Hartman et al. |
| 5,156,610 A | | 10/1992 | Reger et al. |
| 5,158,564 A | | 10/1992 | Schnepp-Pesch |
| 5,170,802 A | | 12/1992 | Mehra |
| 5,178,620 A | | 1/1993 | Eggers et al. |
| 5,178,625 A | | 1/1993 | Groshong et al. |
| 5,190,540 A | | 3/1993 | Lee |
| 5,211,651 A | | 5/1993 | Reger et al. |
| 5,234,407 A | | 8/1993 | Teirstein et al. |
| 5,242,441 A | | 9/1993 | Avitall |
| 5,251,634 A | | 10/1993 | Weinberg et al. |
| 5,255,679 A | | 10/1993 | Imran |
| 5,263,493 A | | 11/1993 | Avitall |
| 5,267,954 A | | 12/1993 | Nita et al. |
| 5,277,201 A | | 1/1994 | Stern et al. |
| 5,282,484 A | | 2/1994 | Reger et al. |
| 5,286,254 A | | 2/1994 | Shapland et al. |
| 5,295,484 A | | 3/1994 | Marcus |
| 5,297,564 A | | 3/1994 | Love et al. |
| 5,300,068 A | | 4/1994 | Rosar et al. |
| 5,301,683 A | | 4/1994 | Durkan |
| 5,304,115 A | | 4/1994 | Pflueger et al. |
| 5,304,121 A | | 4/1994 | Sahatjian |
| 5,304,171 A | | 4/1994 | Gregory et al. |
| 5,304,173 A | | 4/1994 | Kittrell et al. |
| 5,306,250 A | | 4/1994 | March et al. |
| 5,312,328 A | | 5/1994 | Nita et al. |
| 5,314,466 A | | 5/1994 | Stern et al. |
| 5,322,064 A | | 6/1994 | Lundquist |
| 5,324,255 A | | 6/1994 | Passafaro et al. |
| 5,326,341 A | | 7/1994 | Lew et al. |
| 5,326,342 A | | 7/1994 | Pflueger et al. |
| 5,330,518 A | | 7/1994 | Neilson et al. |
| 5,333,614 A | | 8/1994 | Feiring |
| 5,342,292 A | | 8/1994 | Nita et al. |
| 5,344,395 A | | 9/1994 | Whalen et al. |
| 5,364,392 A | | 11/1994 | Warner et al. |
| 5,365,172 A | | 11/1994 | Hrovat et al. |
| 5,368,557 A | | 11/1994 | Nita et al. |
| 5,368,558 A | | 11/1994 | Nita et al. |
| 5,380,274 A | | 1/1995 | Nita et al. |
| 5,380,319 A | | 1/1995 | Saito et al. |
| 5,382,228 A | | 1/1995 | Nita et al. |
| 5,383,874 A | | 1/1995 | Jackson et al. |
| 5,383,917 A | | 1/1995 | Desai et al. |
| 5,397,301 A | | 3/1995 | Pflueger et al. |
| 5,397,339 A | | 3/1995 | Desai |
| 5,401,272 A | | 3/1995 | Perkins et al. |
| 5,403,311 A | | 4/1995 | Abele et al. |
| 5,405,318 A | | 4/1995 | Nita et al. |
| 5,405,346 A | | 4/1995 | Grundy et al. |
| 5,409,000 A | | 4/1995 | Imran |
| 5,417,672 A | | 5/1995 | Nita et al. |
| 5,419,767 A | | 5/1995 | Eggers et al. |
| 5,427,118 A | | 6/1995 | Nita et al. |
| 5,432,876 A | | 7/1995 | Appeldorn et al. |
| 5,441,498 A | | 8/1995 | Perkins et al. |
| 5,447,509 A | | 9/1995 | Mills et al. |
| 5,451,207 A | | 9/1995 | Yock et al. |
| 5,453,091 A | | 9/1995 | Taylor et al. |
| 5,454,788 A | | 10/1995 | Walker et al. |
| 5,454,809 A | | 10/1995 | Janssen |
| 5,455,029 A | | 10/1995 | Hartman et al. |
| 5,456,682 A | | 10/1995 | Edwards et al. |
| 5,457,042 A | | 10/1995 | Hartman et al. |
| 5,471,982 A | | 12/1995 | Edwards et al. |
| 5,474,530 A | | 12/1995 | Passafaro et al. |
| 5,478,351 A | | 12/1995 | Meade et al. |
| 5,496,311 A | | 3/1996 | Abele et al. |
| 5,496,312 A | | 3/1996 | Klicek et al. |
| 5,498,261 A | | 3/1996 | Strul |
| 5,505,201 A | | 4/1996 | Grill et al. |
| 5,505,730 A | | 4/1996 | Edwards |
| 5,507,744 A | | 4/1996 | Tay et al. |
| 5,522,873 A | | 6/1996 | Jackman et al. |
| 5,531,520 A | | 7/1996 | Grimson et al. |
| 5,540,656 A | | 7/1996 | Pflueger et al. |
| 5,540,679 A | | 7/1996 | Fram et al. |
| 5,540,681 A | | 7/1996 | Strul et al. |
| 5,542,917 A | | 8/1996 | Nita et al. |
| 5,545,161 A | | 8/1996 | Imran |
| 5,562,100 A | | 10/1996 | Kittrell et al. |
| 5,571,122 A | | 11/1996 | Kelly et al. |
| 5,571,151 A | | 11/1996 | Gregory |
| 5,573,531 A | | 11/1996 | Gregory |
| 5,573,533 A | | 11/1996 | Strul |
| 5,584,831 A | | 12/1996 | McKay |
| 5,584,872 A | | 12/1996 | Lafontaine et al. |
| 5,588,962 A | | 12/1996 | Nicholas et al. |
| 5,599,346 A | | 2/1997 | Edwards et al. |
| 5,601,526 A | | 2/1997 | Chapelon et al. |
| 5,609,606 A | | 3/1997 | O'Boyle et al. |

(56) References Cited

U.S. PATENT DOCUMENTS

| | | |
|---|---|---|
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy-Chutorian et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | LaFontaine et al. |
| 5,904,651 A | 5/1999 | Swanson et al. |
| 5,904,667 A | 5/1999 | Falwell |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells, III et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy-Chutorian et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |

(56) References Cited

U.S. PATENT DOCUMENTS

| | | |
|---|---|---|
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger |
| 6,168,594 B1 | 1/2001 | LaFontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |

(56) References Cited

U.S. PATENT DOCUMENTS

| | | |
|---|---|---|
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung |
| 6,602,246 B1 | 8/2003 | Joye et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |

(56) References Cited

U.S. PATENT DOCUMENTS

| | | |
|---|---|---|
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison et al. |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |

(56) References Cited

U.S. PATENT DOCUMENTS

| | | |
|---|---|---|
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |

(56) References Cited

U.S. PATENT DOCUMENTS

| | | |
|---|---|---|
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais et al. |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 8,758,339 B2 * | 6/2014 | Bee et al. .......... 606/41 |
| 2001/0007070 A1 | 7/2001 | Stewart et al. |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0065317 A1 | 4/2003 | Rudie et al. |
| 2003/0092995 A1 | 5/2003 | Thompson |

(56) References Cited

U.S. PATENT DOCUMENTS

| | | |
|---|---|---|
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0080374 A1 | 4/2005 | Esch et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward et al. |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0142801 A1 | 6/2006 | Demarais et al. |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184221 A1 | 8/2006 | Stewart et al. |
| 2006/0189896 A1* | 8/2006 | Davis et al. .................. 600/585 |
| 2006/0195139 A1 | 8/2006 | Gertner |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0265014 A1 | 11/2006 | Demarais et al. |
| 2006/0265015 A1 | 11/2006 | Demarais et al. |
| 2006/0269555 A1 | 11/2006 | Salcedo et al. |
| 2006/0271111 A1 | 11/2006 | Demarais et al. |
| 2006/0276852 A1 | 12/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066957 A1 | 3/2007 | Demarais et al. |
| 2007/0066972 A1 | 3/2007 | Ormsby et al. |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0173899 A1 | 7/2007 | Levin et al. |
| 2007/0179496 A1 | 8/2007 | Swoyer et al. |
| 2007/0203480 A1 | 8/2007 | Mody et al. |
| 2007/0203549 A1 | 8/2007 | Demarais et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |

(56) References Cited

U.S. PATENT DOCUMENTS

| | | |
|---|---|---|
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1* | 10/2008 | Zarins et al. .......... 607/99 |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018566 A1* | 1/2009 | Escudero et al. .......... 606/159 |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221939 A1 | 9/2009 | Demarais et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0057150 A1 | 3/2010 | Demarais et al. |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Demarais et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |

(56) References Cited

U.S. PATENT DOCUMENTS

| | | |
|---|---|---|
| 2011/0166499 A1 | 7/2011 | Demarais et al. |
| 2011/0178570 A1 | 7/2011 | Demarais et al. |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramaniam et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |

FOREIGN PATENT DOCUMENTS

| | | |
|---|---|---|
| EP | 1180004 A1 | 2/2002 |
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 0047118 A1 | 8/2000 |
| WO | 03026525 A1 | 4/2003 |
| WO | 2004100813 A2 | 11/2004 |
| WO | 2004110258 A2 | 12/2004 |
| WO | WO2006022790 | 3/2006 |
| WO | WO2006041881 | 4/2006 |
| WO | 2006105121 A2 | 10/2006 |
| WO | WO2007035537 | 3/2007 |
| WO | WO2007078997 | 7/2007 |
| WO | WO2007086965 | 8/2007 |
| WO | WO2007103879 | 9/2007 |
| WO | WO2007103881 | 9/2007 |
| WO | WO2007121309 | 10/2007 |
| WO | WO2007146834 | 12/2007 |

(56) References Cited

FOREIGN PATENT DOCUMENTS

| WO | 2008014465 A2 | 1/2008 |
|---|---|---|
| WO | WO2008003058 | 1/2008 |
| WO | WO2008061150 | 5/2008 |
| WO | WO2008061152 | 5/2008 |
| WO | WO2008070413 | 6/2008 |
| WO | 2009121017 A1 | 10/2009 |
| WO | 2010067360 A2 | 6/2010 |
| WO | WO2010078175 | 7/2010 |
| WO | 2010102310 A2 | 9/2010 |
| WO | WO2010129661 | 11/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | WO2011091069 | 7/2011 |
| WO | 2011130534 A2 | 10/2011 |
| WO | WO2011130005 | 10/2011 |
| WO | WO2011139589 | 11/2011 |
| WO | 2012019156 A1 | 2/2012 |
| WO | WO2012019156 | 2/2012 |
| WO | 2013049601 A2 | 4/2013 |

OTHER PUBLICATIONS

U.S. Appl. No. 13/086,116, filed Apr. 13, 2011, Hastings et al.
U.S. Appl. No. 12/980,972, filed Dec. 29, 2010, Vrba et al.
U.S. Appl. No. 13/157,844, filed Jun. 10, 2011, Hastings et al.
U.S. Appl. No. 13/087,163, filed Apr. 14, 2011, Ingle.
U.S. Appl. No. 13/086,121, filed Apr. 13, 2011, Hastings et al.
CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18.
Zhou et al., "Mechanism Research of Cryoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Omura et al., "A Mild Acute Compression Induces Neurapraxia in Rat Sciatic Nerve," The International Journal of Neuroscience, vol. 114 (12), pp. 1561-1572.
Baun, "Interaction with Soft Tissue," Principles of General & Vascular Sonography, Chapter 2, pp. 23-24, Before Mar. 2012.
Blue Cross Blue Shield Medicaly Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.

Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
US 8,398,630, 3/2013, Demarais et al. (withdrawn).
Van Den Berg, "Light echoes image the human body," OLE, Oct. 2001, p. 35-37.
"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: Advantages of OCT," LightLab Imaging Technology.
"Optical Coherence Tomography: Image Gallery Cardiovascular Procedures," LightLab Imaging Technology.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Optical Coherence Tomography: What is OCT?," LightLab Imaging Technology.
"Optical Coherence Tomography: Why Use OCT?," LightLab Imaging Technology.
"Products—Functional Measurement," VOLCANO Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-6.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.

(56) References Cited

OTHER PUBLICATIONS

Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.
Popma et al., "Percutaneous Coronary and Valvular Intervention," p. 1364-1405.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.
Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.

\* cited by examiner

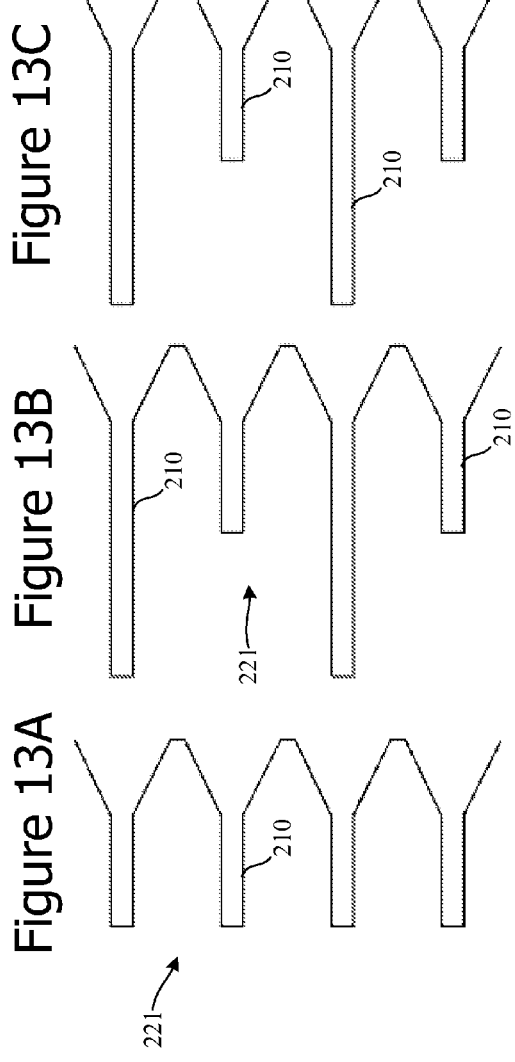
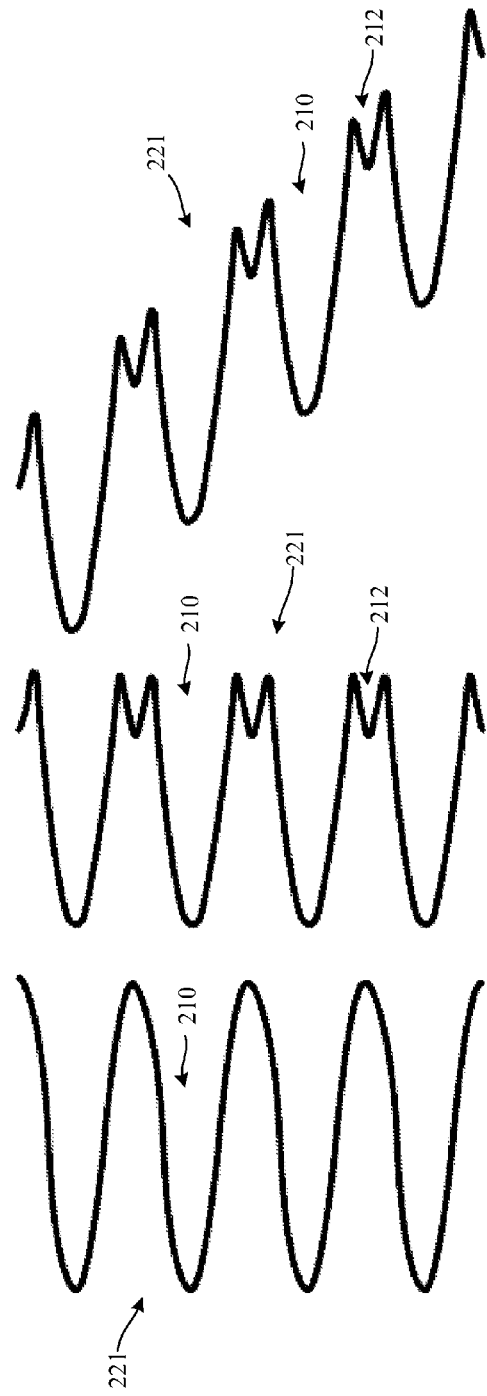
Figure 13A  Figure 13B  Figure 13C
Figure 14A  Figure 14B  Figure 14C

PRECISION ELECTRODE MOVEMENT CONTROL FOR RENAL NERVE ABLATION

RELATED APPLICATIONS

This application claims the benefit of Provisional Patent Application Ser. No. 61/369,463 filed Jul. 30, 2010, to which priority is claimed pursuant to 35 U.S.C. §119(e) and which is hereby incorporated herein by reference.

SUMMARY

Embodiments of the disclosure are directed to control mechanisms situated at a distal end of an elongated flexible member that provide for precision movement of a component coupled to a distal end or other portion of the control mechanism. Embodiments of the disclosure are directed to control mechanisms situated at a distal end of an elongated flexible member dimensioned for deployment within a vessel of the body that provide for precision movement of a component coupled to a distal end or other portion of the control mechanism. Various embodiments are directed to a position converter situated at a distal end of a catheter and configured to convert movement of a proximal actuation member into one or both of controlled rotational movement and controlled axial movement of a component coupled to a distal end of the position converter substantially free of one or more of elastic deformation, friction, and whip impacting actuation member movement. Various embodiments are directed to a position converter situated at a distal end of a catheter and configured to convert movement of a proximal actuation member into one or both of controlled rotational movement and controlled axial movement of a component coupled to a distal end of the position converter to one of a plurality of stable circumferential and/or axial positions.

The position converter may comprise various types of orientation, positioning, and/or indexing components. For example, in some embodiments, the position converter may comprise a ratcheting arrangement configured to convert axial movement of a proximal actuation member into one or both of controlled rotational movement and controlled axial movement of a component coupled to the distal end of the position converter. In other embodiments, the position converter may comprise a magnetic indexing arrangement configured to magnetically urge a component coupled to the distal end of the position converter to one of a plurality of stable circumferential and/or axial positions. In further embodiments, the position converter may comprise a geometric keyed orientation mechanism configured to guide a key component of a proximal actuation member into and along a keyway arrangement that limits movement of a component coupled to the distal end of the position converter to one of a plurality of stable circumferential positions and/or stable axial positions. The component coupled to the distal end of the position converter may comprise a medical device, such as a sensor, an electrode, an ablation device, or other medical instrument. The component may comprise, for example, an ablation electrode or other type of ablation device, such as an ultrasound, laser, microwave, or thermal ablation device, configured for one or both of ablation and monitoring/imaging.

Embodiments of the disclosure are generally directed to apparatuses and methods for ablating target tissue of the body from within a vessel. Embodiments are directed to high frequency AC ablation catheters, systems, and methods that employ a control mechanism for moving an electrode during ablation with precision. Various embodiments of the disclosure are directed to apparatuses and methods for ablating perivascular renal nerves, such as for the treatment of hypertension.

According to various embodiments, an apparatus includes a catheter comprising a flexible shaft having a proximal end, a distal end, a length, and a lumen extending between the proximal and distal ends. The length of the shaft is sufficient to access a location within the body at or proximate target tissue to be ablated. A flexible actuation member is provided within the lumen of the shaft and extends between the shaft's proximal and distal ends. The actuation member is moveable within the lumen of the shaft and subject to one or more of elastic deformation, friction, and whip along its length during movement within the shaft's lumen. A flexible support is coupled to a distal end of the actuation member and extendible beyond a distal tip of the shaft. An electrode is provided at a distal end of the support member and configured to contact tissue at or near the target tissue.

The electrode is configured to deliver high frequency AC energy sufficient to ablate the target tissue proximate the electrode. The support member is configured to maintain a desired position of the electrode. A position converter is provided at the distal end of the shaft and configured to convert movement of the actuation member into at least controlled rotational movement of the support member and the electrode to one of a plurality of stable circumferential positions substantially free of the one or more of elastic deformation, friction, and whip impacting actuation member movement. In some embodiments, the position converter is configured to convert axial movement of the actuation member, which is subject to elastic deformation, friction, and whip, into controlled axial movement of the support member and the electrode to one of a plurality of stable axial positions.

In accordance with various embodiments, a catheter includes a flexible shaft having a proximal end, a distal end, a length, and a lumen extending between the proximal and distal ends. The length of the shaft is sufficient to access a patient's renal artery relative to a percutaneous access location. A flexible actuation member is provided within the lumen and extends between the proximal and distal ends of the shaft. The actuation member is moveable within the lumen of the shaft and subject to one or more of elastic deformation, friction, and whip along its length during movement within the shaft's lumen. A flexible support is provided at a distal end of the actuation member and extendible beyond a distal tip of the shaft and into a lumen of the renal artery. An electrode is provided at a distal end of the support member and configured to contact an inner wall of the renal artery and deliver high frequency AC energy sufficient to ablate perivascular renal nerve tissue proximate the electrode. The support member is configured to urge the electrode into contact with the inner wall of the renal artery.

A position converter is provided at the distal end of the shaft and configured to convert movement of the actuation member into at least controlled rotational movement of the support member and the electrode to one of a plurality of stable circumferential positions substantially free of the one or more of elastic deformation, friction, and whip impacting actuation member movement. In some embodiments, the position converter is configured to convert axial movement of the actuation member, which is subject to elastic deformation, friction, and whip, into controlled axial movement of the support member and the electrode to one of a plurality of stable axial positions.

According to some embodiments, the position converter includes a ratcheting arrangement configured to mechanically convert axial movement of the actuation member into controlled rotational movement of the support member and the electrode to one of the plurality of stable circumferential and/or axial positions. In other embodiments, the position converter includes a magnetic indexing arrangement configured to magnetically urge the support member and the electrode to one of the plurality of stable circumferential and/or axial positions. In further embodiments, the position converter includes a geometric keyed orientation mechanism configured to guide a key component of the support member into and along a keyway arrangement that limits movement of the support member and the electrode to one of the plurality of stable circumferential and/or axial positions.

In accordance with various embodiments, a catheter includes a flexible shaft having a proximal end, a distal end, a length, and a lumen extending between the proximal and distal ends. The length of the shaft is sufficient to access target tissue of the body. A slotted tube includes a proximal end, a distal end, and a length extending between the proximal and distal ends sufficient to access the target tissue. The slotted tube is dimensioned for displacement within the lumen of the shaft. The slotted tube includes a plurality of regions defined along the length of the slotted tube having disparate slot patterns associated with disparate mechanical properties including torque transmission and bending flexibility.

In some embodiments, an electrical conductor arrangement extends along the length of the slotted tube. An electrode arrangement is provided at the distal end of the slotted tube and coupled to the conductor arrangement. The electrode arrangement is configured to deliver high frequency AC energy sufficient to ablate the target tissue. In other embodiments, different types of components may be situated at the distal end of the slotted tube and provided with appropriate conductors/couplings, such as a medical device, a sensor, an electrode, an ablation device, or other medical instrument. Representative examples of components that may be situated at the distal end of the slotted tube include, for example, an ultrasound, laser, microwave, or thermal energy transfer device, some of which can be configured for one or both of ablation and monitoring/imaging.

According to some embodiments, a catheter includes a flexible shaft having a proximal end, a distal end, a length, and a lumen extending between the proximal and distal ends. The length of the shaft is sufficient to access a patient's renal artery relative to a percutaneous access location. A slotted tube includes a proximal end, a distal end, and a length extending between the proximal and distal ends sufficient to access the patient's renal artery relative to the percutaneous access location. The slotted tube is dimensioned for displacement within the lumen of the shaft and includes a plurality of regions defined along its length having disparate slot patterns associated with disparate mechanical properties including torque transmission and bending flexibility. An electrical conductor arrangement extends along the length of the slotted tube. An electrode arrangement is provided at the distal end of the slotted tube and coupled to the conductor arrangement. The electrode arrangement is configured to deliver high frequency AC energy sufficient to ablate perivascular renal nerve tissue proximate the renal artery.

Embodiments are directed to methods of ablating target tissue involving advancing an ablation electrode of an ablation catheter to a location of the body at or near target tissue to be ablated. The ablation electrode is provided at a distal end of a flexible support member. The support member is coupled to a position converter situated at a distal end of the catheter. Also coupled to the position converter is a flexible actuation member that extends from the distal end of the catheter to its proximal end. Movement of the support member and the electrode is effected by movement of the actuation member at the proximal end of the catheter, typically by a clinician or robotic system. Movement of the actuation member within the catheter's shaft is subject to one or more of elastic deformation, friction, and whip which can adversely impact control of electrode movement at or near the target tissue. Methods of the disclosure involve converting movement of the actuation member, which is adversely impacted by one or more of elastic deformation, friction, and whip, into controlled rotational movement and/or controlled axial displacement which is substantially free of any such elastic deformation, friction, and/or whip.

Methods involve controlling electrode rotation during ablation to one of a plurality of predetermined stable circumferential positions, which eliminates any adverse impact of elastic deformation, friction, and/or whip impacting movement of an actuation member at the proximal end of the catheter. Methods may also involve controlling electrode axial displacement during ablation to one of a plurality of predetermined stable axial positions, which eliminates any adverse impact of elastic deformation, friction, and or whip impacting movement of the actuation member.

These and other features can be understood in view of the following detailed discussion and the accompanying drawings.

BRIEF DESCRIPTION OF THE DRAWINGS

FIGS. 13A-14C show various views of a keyway having various configurations in accordance with various embodiments;

DISCLOSURE

Figure 1:
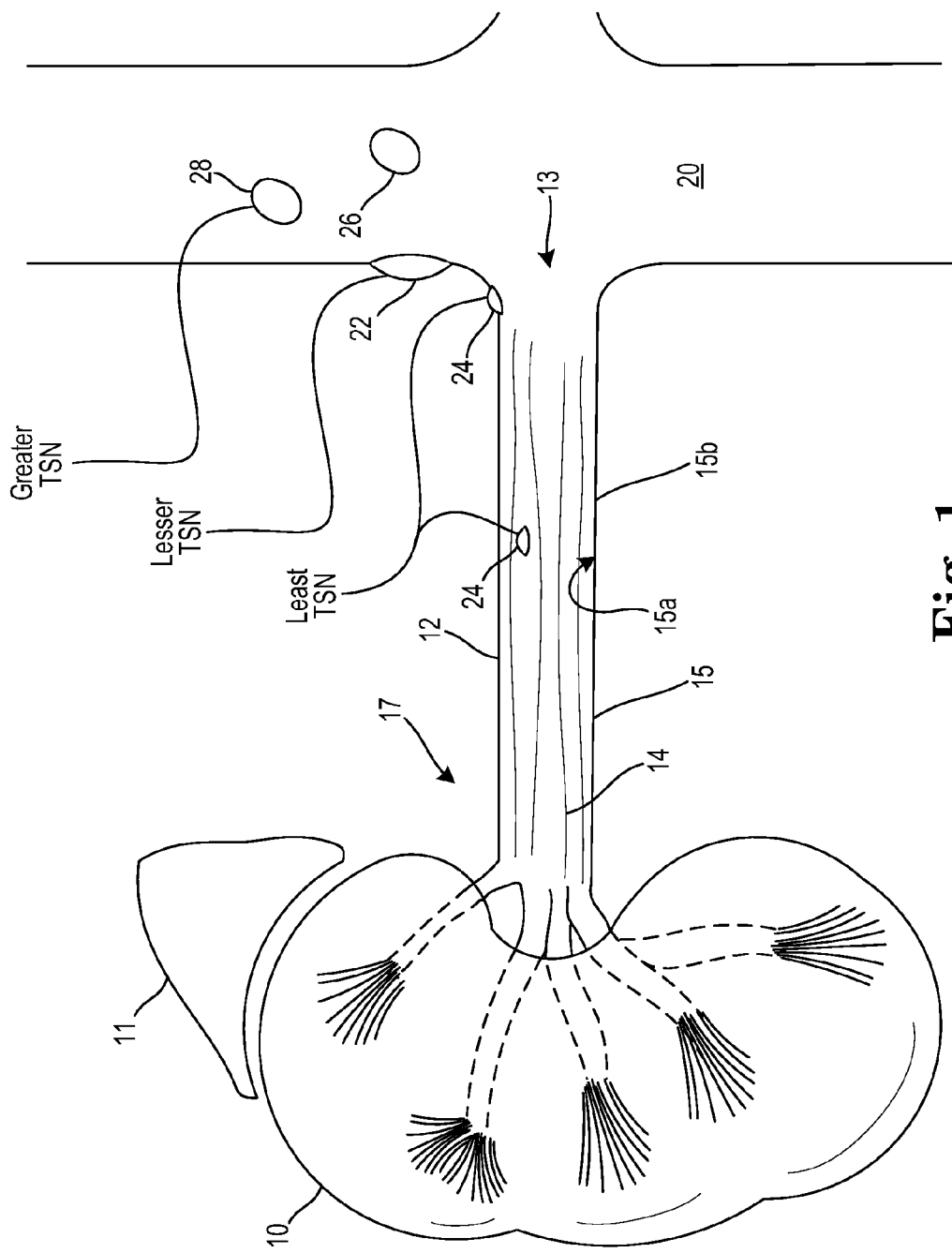
FIG. 1 is an illustration of a right kidney and renal vasculature including a renal artery branching laterally from the abdominal aorta.

Embodiments of the disclosure are directed to apparatuses and methods for ablating target tissue of the body. Embodiments of the disclosure are directed to apparatuses and methods for controlling the movement of an ablation electrode during ablation with precision. Embodiments of the disclosure are directed to apparatuses and methods for ablating perivascular renal nerves from within the renal artery using a precision electrode movement control apparatus for the treatment of hypertension.

Ablation of perivascular renal nerves can be an effective treatment for hypertension. Radiofrequency (RF) electrodes placed in the renal artery can be used to ablate the renal nerves, but with risk of injury to the artery wall. To control injury to the artery wall, one approach is to ablate at discrete locations along and around the artery. However, reliable control of electrode position has been difficult, which is adversely impacted by catheter or electrode "whip" as the electrode is moved around in the artery, for example. Also, precise control of the proximal hub of conventional ablation devices may not translate into correspondingly precise control of the tip, due to flexibility, curves, friction, and so forth. Embodiments of the disclosure provide a more precise way of controlling electrode position to desired locations in the renal artery, for example.

Various embodiments of the disclosure are directed to apparatuses and methods for renal denervation for treating hypertension. Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Deactivation of nerves in the kidneys via renal denervation can reduce blood pressure, and may be a viable treatment option for many patients with hypertension who do not respond to conventional drugs.

The kidneys are instrumental in a number of body processes, including blood filtration, regulation of fluid balance, blood pressure control, electrolyte balance, and hormone production. One primary function of the kidneys is to remove toxins, mineral salts, and water from the blood to form urine. The kidneys receive about 20-25% of cardiac output through the renal arteries that branch left and right from the abdominal aorta, entering each kidney at the concave surface of the kidneys, the renal hilum.

Blood flows into the kidneys through the renal artery and the afferent arteriole, entering the filtration portion of the kidney, the renal corpuscle. The renal corpuscle is composed of the glomerulus, a thicket of capillaries, surrounded by a fluid-filled, cup-like sac called Bowman's capsule. Solutes in the blood are filtered through the very thin capillary walls of the glomerulus due to the pressure gradient that exists between the blood in the capillaries and the fluid in the Bowman's capsule. The pressure gradient is controlled by the contraction or dilation of the arterioles. After filtration occurs, the filtered blood moves through the efferent arteriole and the peritubular capillaries, converging in the interlobular veins, and finally exiting the kidney through the renal vein.

Particles and fluid filtered from the blood move from the Bowman's capsule through a number of tubules to a collecting duct. Urine is formed in the collecting duct and then exits through the ureter and bladder. The tubules are surrounded by the peritubular capillaries (containing the filtered blood). As the filtrate moves through the tubules and toward the collecting duct, nutrients, water, and electrolytes, such as sodium and chloride, are reabsorbed into the blood.

The kidneys are innervated by the renal plexus which emanates primarily from the aorticorenal ganglion. Renal ganglia are formed by the nerves of the renal plexus as the nerves follow along the course of the renal artery and into the kidney. The renal nerves are part of the autonomic nervous system which includes sympathetic and parasympathetic components. The sympathetic nervous system is known to be the system that provides the bodies "fight or flight" response, whereas the parasympathetic nervous system provides the "rest and digest" response. Stimulation of sympathetic nerve activity triggers the sympathetic response which causes the kidneys to increase production of hormones that increase vasoconstriction and fluid retention. This process is referred to as the renin-angiotensin-aldosterone-system (RAAS) response to increased renal sympathetic nerve activity.

In response to a reduction in blood volume, the kidneys secrete renin, which stimulates the production of angiotensin. Angiotensin causes blood vessels to constrict, resulting in increased blood pressure, and also stimulates the secretion of the hormone aldosterone from the adrenal cortex. Aldosterone causes the tubules of the kidneys to increase the reabsorption of sodium and water, which increases the volume of fluid in the body and blood pressure.

Congestive heart failure (CHF) is a condition that has been linked to kidney function. CHF occurs when the heart is unable to pump blood effectively throughout the body. When blood flow drops, renal function degrades because of insufficient perfusion of the blood within the renal corpuscles. The decreased blood flow to the kidneys triggers an increase in sympathetic nervous system activity (i.e., the RAAS becomes too active) that causes the kidneys to secrete hormones that increase fluid retention and vasorestriction. Fluid retention and vasorestriction in turn increases the peripheral resistance of the circulatory system, placing an even greater load on the heart, which diminishes blood flow further. If the deterioration in cardiac and renal functioning continues, eventually the body becomes overwhelmed, and an episode of heart failure decompensation occurs, often leading to hospitalization of the patient.

FIG. 1 is an illustration of a right kidney 10 and renal vasculature including a renal artery 12 branching laterally from the abdominal aorta 20. In FIG. 1, only the right kidney 10 is shown for purposes of simplicity of explanation, but reference will be made herein to both right and left kidneys and associated renal vasculature and nervous system structures, all of which are contemplated within the context of embodiments of the disclosure. The renal artery 12 is purposefully shown to be disproportionately larger than the right kidney 10 and abdominal aorta 20 in order to facilitate discussion of various features and embodiments of the present disclosure.

The right and left kidneys are supplied with blood from the right and left renal arteries that branch from respective right and left lateral surfaces of the abdominal aorta 20. Each of the right and left renal arteries is directed across the crus of the diaphragm, so as to form nearly a right angle with the abdominal aorta 20. The right and left renal arteries extend generally from the abdominal aorta 20 to respective renal sinuses proximate the hilum 17 of the kidneys, and branch into segmental arteries and then interlobular arteries within the kidney 10. The interlobular arteries radiate outward, penetrating the renal capsule and extending through the renal columns between the renal pyramids. Typically, the kidneys receive about 20% of total cardiac output which, for normal persons, represents about 1200 mL of blood flow through the kidneys per minute.

The primary function of the kidneys is to maintain water and electrolyte balance for the body by controlling the production and concentration of urine. In producing urine, the kidneys excrete wastes such as urea and ammonium. The kidneys also control reabsorption of glucose and amino acids, and are important in the production of hormones including vitamin D, renin and erythropoietin.

An important secondary function of the kidneys is to control metabolic homeostasis of the body. Controlling hemostatic functions include regulating electrolytes, acid-base balance, and blood pressure. For example, the kidneys are responsible for regulating blood volume and pressure by adjusting volume of water lost in the urine and releasing erythropoietin and renin, for example. The kidneys also regulate plasma ion concentrations (e.g., sodium, potassium, chloride ions, and calcium ion levels) by controlling the quantities lost in the urine and the synthesis of calcitrol. Other hemostatic functions controlled by the kidneys include stabilizing blood pH by controlling loss of hydrogen and bicarbonate ions in the urine, conserving valuable nutrients by preventing their excretion, and assisting the liver with detoxification.

Also shown in FIG. 1 is the right suprarenal gland 11, commonly referred to as the right adrenal gland. The suprarenal gland 11 is a star-shaped endocrine gland that rests on top of the kidney 10. The primary function of the suprarenal glands (left and right) is to regulate the stress response of the body through the synthesis of corticosteroids and catecholamines, including cortisol and adrenaline (epinephrine), respectively. Encompassing the kidneys 10, suprarenal glands 11, renal vessels 12, and adjacent perirenal fat is the renal fascia, e.g., Gerota's fascia, (not shown), which is a fascial pouch derived from extraperitoneal connective tissue.

The autonomic nervous system of the body controls involuntary actions of the smooth muscles in blood vessels, the digestive system, heart, and glands. The autonomic nervous system is divided into the sympathetic nervous system and the parasympathetic nervous system. In general terms, the parasympathetic nervous system prepares the body for rest by lowering heart rate, lowering blood pressure, and stimulating digestion. The sympathetic nervous system effectuates the body's fight-or-flight response by increasing heart rate, increasing blood pressure, and increasing metabolism.

In the autonomic nervous system, fibers originating from the central nervous system and extending to the various ganglia are referred to as preganglionic fibers, while those extending from the ganglia to the effector organ are referred to as postganglionic fibers. Activation of the sympathetic nervous system is effected through the release of adrenaline (epinephrine) and to a lesser extent norepinephrine from the suprarenal glands 11. This release of adrenaline is triggered by the neurotransmitter acetylcholine released from preganglionic sympathetic nerves.

Figure 2A:
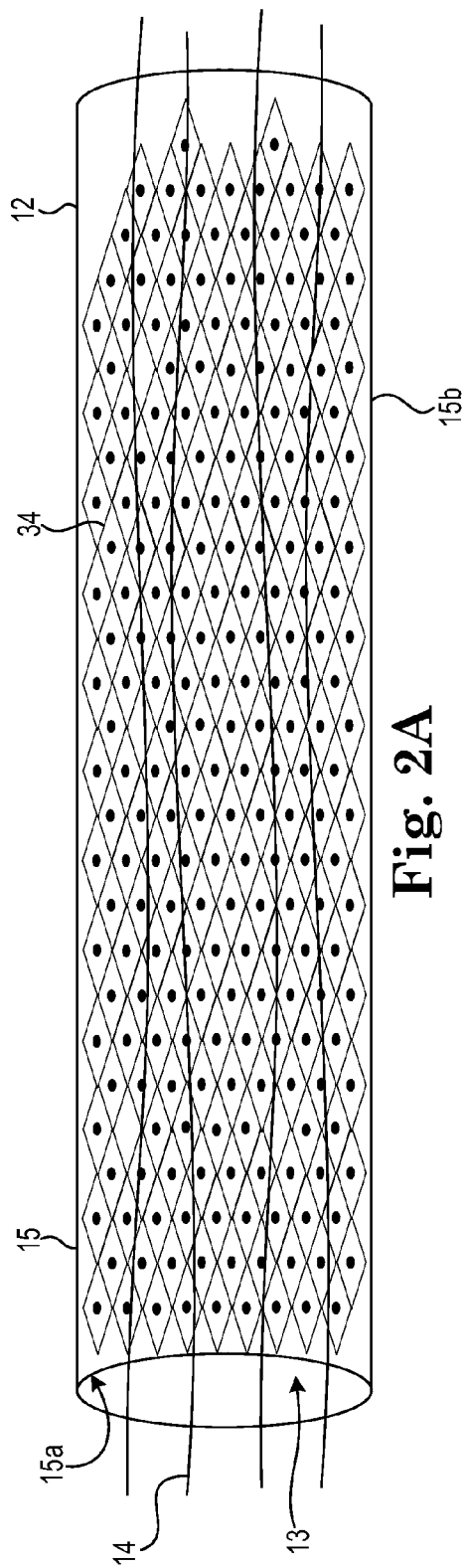
FIGS. 2A and 2B illustrate sympathetic innervation of the renal artery.
Figure 2B:
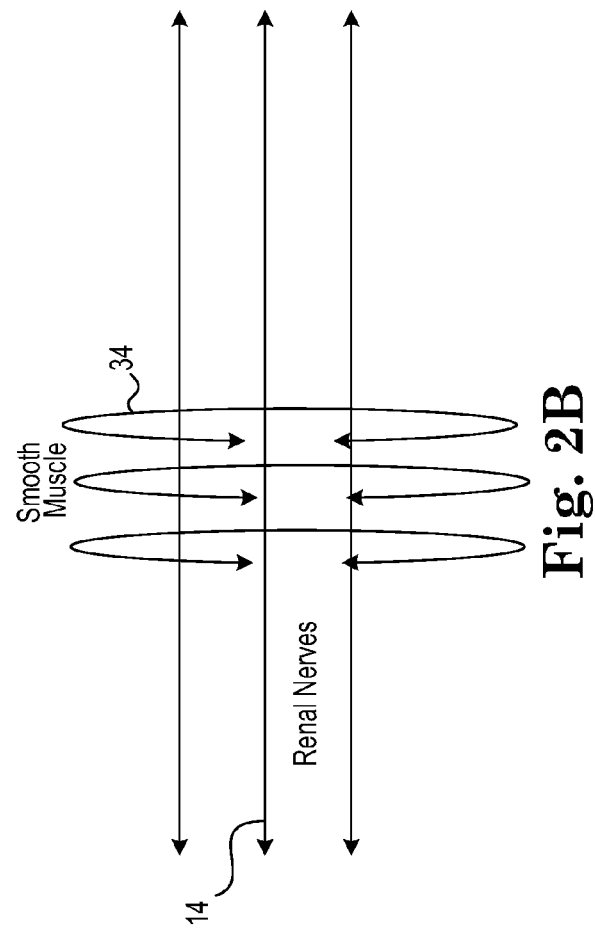

The kidneys and ureters (not shown) are innervated by the renal nerves 14. FIGS. 1 and 2A-2B illustrate sympathetic innervation of the renal vasculature, primarily innervation of the renal artery 12. The primary functions of sympathetic innervation of the renal vasculature include regulation of renal blood flow and pressure, stimulation of renin release, and direct stimulation of water and sodium ion reabsorption.

Most of the nerves innervating the renal vasculature are sympathetic postganglionic fibers arising from the superior mesenteric ganglion 26. The renal nerves 14 extend generally axially along the renal arteries 12, enter the kidneys 10 at the hilum 17, follow the branches of the renal arteries 12 within the kidney 10, and extend to individual nephrons. Other renal ganglia, such as the renal ganglia 24, superior mesenteric ganglion 26, the left and right aorticorenal ganglia 22, and celiac ganglia 28 also innervate the renal vasculature. The celiac ganglia 28 is joined by the greater thoracic splanchnic nerve (greater TSN). The aorticorenal ganglia 26 is joined by the lesser thoracic splanchnic nerve (lesser TSN) and innervates the greater part of the renal plexus.

Sympathetic signals to the kidney 10 are communicated via innervated renal vasculature that originates primarily at spinal segments T10-T12 and L1. Parasympathetic signals originate primarily at spinal segments S2-S4 and from the medulla oblongata of the lower brain. Sympathetic nerve traffic travels through the sympathetic trunk ganglia, where some may synapse, while others synapse at the aorticorenal ganglion 22 (via the lesser thoracic splanchnic nerve, i.e., lesser TSN) and the renal ganglion 24 (via the least thoracic splanchnic nerve, i.e., least TSN). The postsynaptic sympathetic signals then travel along nerves 14 of the renal artery 12 to the kidney 10. Presynaptic parasympathetic signals travel to sites near the kidney 10 before they synapse on or near the kidney 10.

With particular reference to FIG. 2A, the renal artery 12, as with most arteries and arterioles, is lined with smooth muscle 34 that controls the diameter of the renal artery lumen 13. Smooth muscle, in general, is an involuntary non-striated muscle found within the media layer of large and small arteries and veins, as well as various organs. The glomeruli of the kidneys, for example, contain a smooth muscle-like cell called the mesangial cell. Smooth muscle is fundamentally different from skeletal muscle and cardiac muscle in terms of structure, function, excitation-contraction coupling, and mechanism of contraction.

Smooth muscle cells can be stimulated to contract or relax by the autonomic nervous system, but can also react on stimuli from neighboring cells and in response to hormones and blood borne electrolytes and agents (e.g., vasodilators or vasoconstrictors). Specialized smooth muscle cells within the afferent arteriole of the juxtaglomerular apparatus of kidney 10, for example, produces renin which activates the angiotension II system.

The renal nerves 14 innervate the smooth muscle 34 of the renal artery wall 15 and extend lengthwise in a generally axial or longitudinal manner along the renal artery wall 15. The smooth muscle 34 surrounds the renal artery circumferentially, and extends lengthwise in a direction generally transverse to the longitudinal orientation of the renal nerves 14, as is depicted in FIG. 2B.

The smooth muscle 34 of the renal artery 12 is under involuntary control of the autonomic nervous system. An increase in sympathetic activity, for example, tends to contract the smooth muscle 34, which reduces the diameter of the renal artery lumen 13 and decreases blood perfusion. A decrease in sympathetic activity tends to cause the smooth muscle 34 to relax, resulting in vessel dilation and an increase in the renal artery lumen diameter and blood perfusion. Conversely, increased parasympathetic activity tends to relax the smooth muscle 34, while decreased parasympathetic activity tends to cause smooth muscle contraction.

Figure 3A:
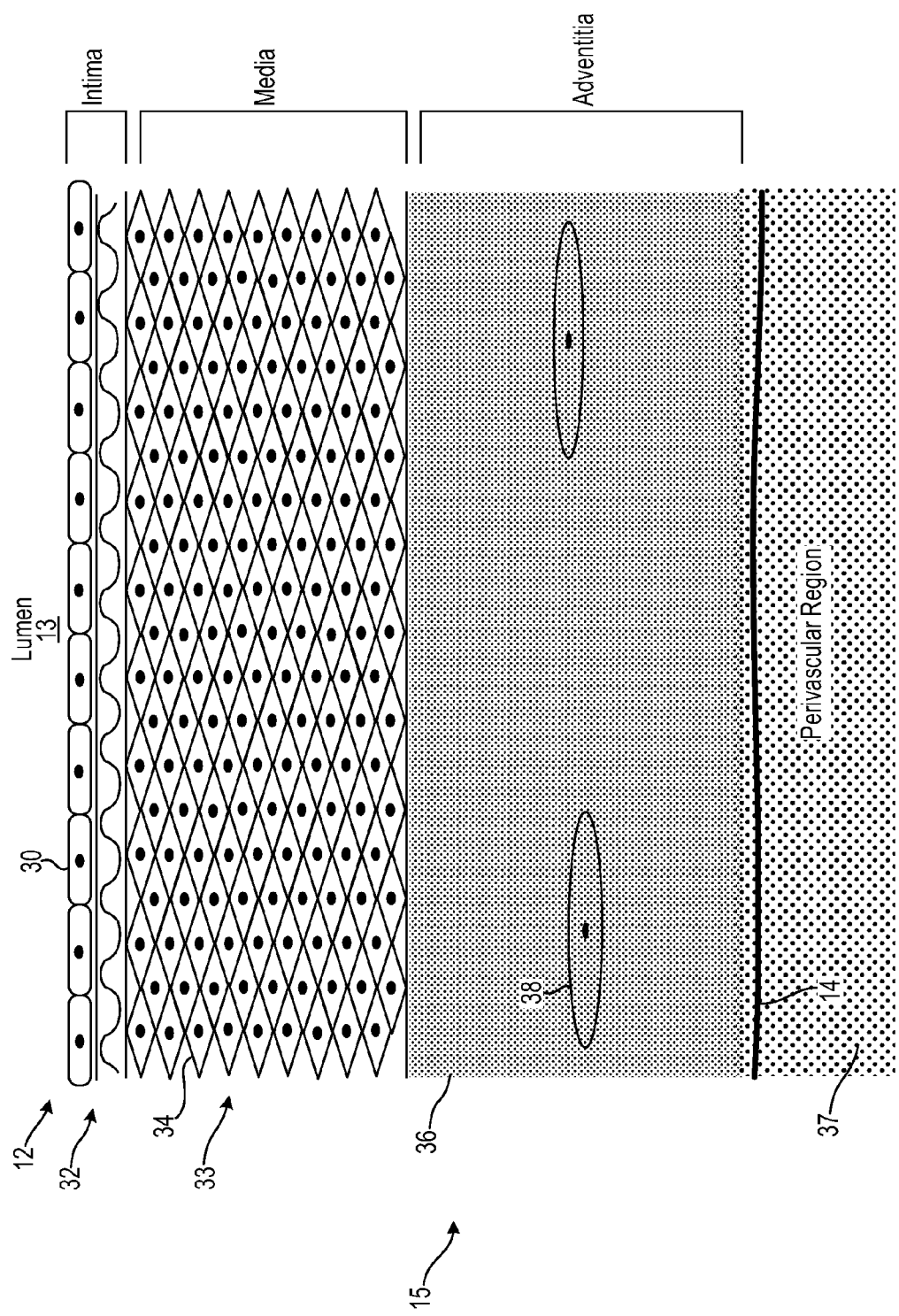
FIG. 3A illustrates various tissue layers of the wall of the renal artery.

FIG. 3A shows a segment of a longitudinal cross-section through a renal artery, and illustrates various tissue layers of the wall 15 of the renal artery 12. The innermost layer of the renal artery 12 is the endothelium 30, which is the innermost layer of the intima 32 and is supported by an internal elastic membrane. The endothelium 30 is a single layer of cells that contacts the blood flowing though the vessel lumen 13. Endothelium cells are typically polygonal, oval, or fusiform, and have very distinct round or oval nuclei. Cells of the endothelium 30 are involved in several vascular functions, including control of blood pressure by way of vasoconstriction and vasodilation, blood clotting, and acting as a barrier layer between contents within the lumen 13 and surrounding tissue, such as the membrane of the intima 32 separating the intima 32 from the media 34, and the adventitia 36. The membrane or maceration of the intima 32 is a fine, transparent, colorless structure which is highly elastic, and commonly has a longitudinal corrugated pattern.

Adjacent the intima 32 is the media 33, which is the middle layer of the renal artery 12. The media is made up of smooth muscle 34 and elastic tissue. The media 33 can be readily identified by its color and by the transverse arrangement of its fibers. More particularly, the media 33 consists principally of bundles of smooth muscle fibers 34 arranged in a thin plate-like manner or lamellae and disposed circularly around the arterial wall 15. The outermost layer of the renal artery wall 15 is the adventitia 36, which is made up of connective tissue. The adventitia 36 includes fibroblast cells 38 that play an important role in wound healing.

A perivascular region 37 is shown adjacent and peripheral to the adventitia 36 of the renal artery wall 15. A renal nerve 14 is shown proximate the adventitia 36 and passing through a portion of the perivascular region 37. The renal nerve 14 is shown extending substantially longitudinally along the outer wall 15 of the renal artery 12. The main trunk of the renal nerves 14 generally lies in or on the adventitia 36 of the renal artery 12, often passing through the perivascular region 37, with certain branches coursing into the media 33 to enervate the renal artery smooth muscle 34.

Embodiments of the disclosure may be implemented to provide varying degrees of denervation therapy to innervated renal vasculature. For example, embodiments of the disclosure may provide for control of the extent and relative permanency of renal nerve impulse transmission interruption achieved by denervation therapy delivered using a treatment apparatus of the disclosure. The extent and relative permanency of renal nerve injury may be tailored to achieve a desired reduction in sympathetic nerve activity (including a partial or complete block) and to achieve a desired degree of permanency (including temporary or irreversible injury).

Figure 3B:
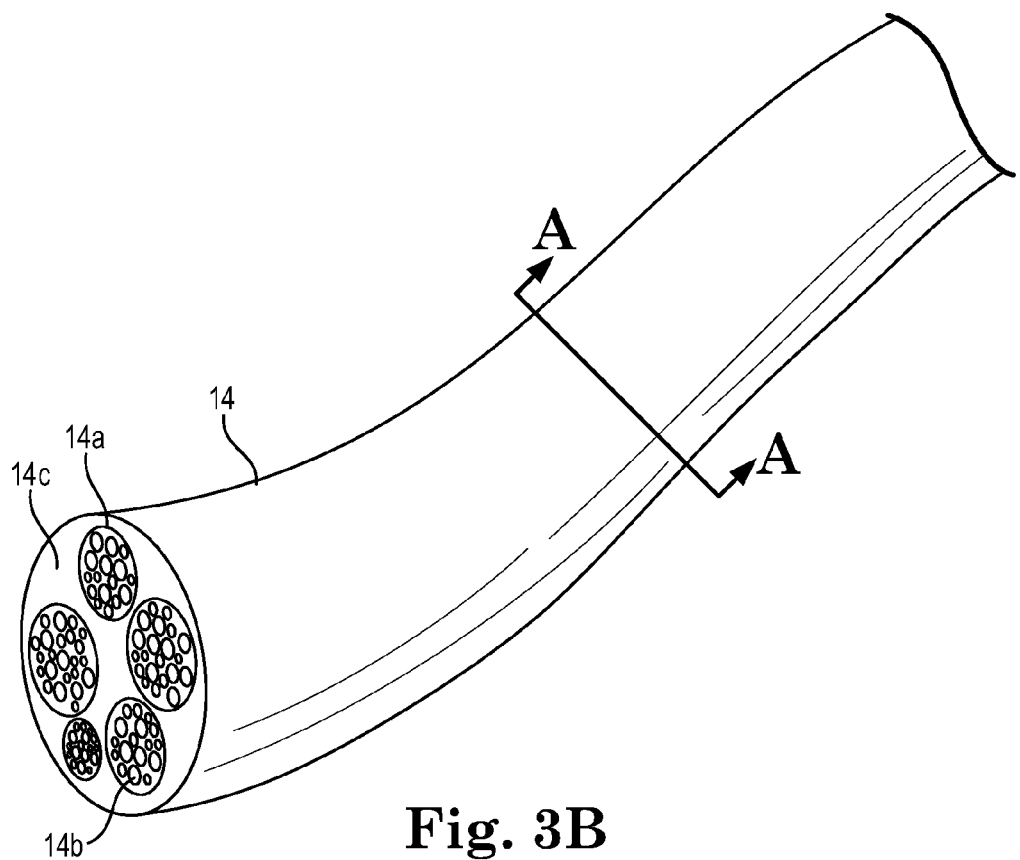
FIGS. 3B and 3C illustrate a portion of a renal nerve.
Figure 3C:
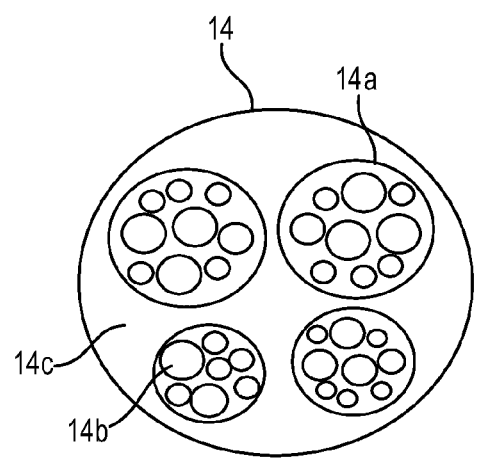

Returning to FIGS. 3B and 3C, the portion of the renal nerve 14 shown in FIGS. 3B and 3C includes bundles 14a of nerve fibers 14b each comprising axons or dendrites that originate or terminate on cell bodies or neurons located in ganglia or on the spinal cord, or in the brain. Supporting tissue structures 14c of the nerve 14 include the endoneurium (surrounding nerve axon fibers), perineurium (surrounds fiber groups to form a fascicle), and epineurium (binds fascicles into nerves), which serve to separate and support nerve fibers 14b and bundles 14a. In particular, the endoneurium, also referred to as the endoneurium tube or tubule, is a layer of delicate connective tissue that encloses the myelin sheath of a nerve fiber 14b within a fasciculus.

Major components of a neuron include the soma, which is the central part of the neuron that includes the nucleus, cellular extensions called dendrites, and axons, which are cable-like projections that carry nerve signals. The axon terminal contains synapses, which are specialized structures where neurotransmitter chemicals are released in order to communicate with target tissues. The axons of many neurons of the peripheral nervous system are sheathed in myelin, which is formed by a type of glial cell known as Schwann cells. The myelinating Schwann cells are wrapped around the axon, leaving the axolemma relatively uncovered at regularly spaced nodes, called nodes of Ranvier. Myelination of axons enables an especially rapid mode of electrical impulse propagation called saltation.

In some embodiments, a treatment apparatus of the disclosure may be implemented to deliver denervation therapy that causes transient and reversible injury to renal nerve fibers 14b. In other embodiments, a treatment apparatus of the disclosure may be implemented to deliver denervation therapy that causes more severe injury to renal nerve fibers 14b, which may be reversible if the therapy is terminated in a timely manner. In preferred embodiments, a treatment apparatus of the disclosure may be implemented to deliver denervation therapy that causes severe and irreversible injury to renal nerve fibers 14b, resulting in permanent cessation of renal sympathetic nerve activity. For example, a treatment apparatus may be implemented to deliver a denervation therapy that disrupts nerve fiber morphology to a degree sufficient to physically separate the endoneurium tube of the nerve fiber 14b, which can prevent regeneration and re-innervation processes.

By way of example, and in accordance with Seddon's classification as is known in the art, a treatment apparatus of the disclosure may be implemented to deliver a denervation therapy that interrupts conduction of nerve impulses along the renal nerve fibers 14b by imparting damage to the renal nerve fibers 14b consistent with neruapraxia. Neurapraxia describes nerve damage in which there is no disruption of the nerve fiber 14b or its sheath. In this case, there is an interruption in conduction of the nerve impulse down the nerve fiber, with recovery taking place within hours to months without true regeneration, as Wallerian degeneration does not occur. Wallerian degeneration refers to a process in which the part of the axon separated from the neuron's cell nucleus degenerates. This process is also known as anterograde degeneration. Neurapraxia is the mildest form of nerve injury that may be imparted to renal nerve fibers 14b by use of a treatment apparatus according to embodiments of the disclosure.

A treatment apparatus may be implemented to interrupt conduction of nerve impulses along the renal nerve fibers 14b by imparting damage to the renal nerve fibers consistent with axonotmesis. Axonotmesis involves loss of the relative continuity of the axon of a nerve fiber and its covering of myelin, but preservation of the connective tissue framework of the nerve fiber. In this case, the encapsulating support tissue 14c of the nerve fiber 14b are preserved. Because axonal continuity is lost, Wallerian degeneration occurs. Recovery from axonotmesis occurs only through regeneration of the axons, a process requiring time on the order of several weeks or months. Electrically, the nerve fiber 14b shows rapid and complete degeneration. Regeneration and re-innervation may occur as long as the endoneural tubes are intact.

A treatment apparatus may be implemented to interrupt conduction of nerve impulses along the renal nerve fibers 14b by imparting damage to the renal nerve fibers 14b consistent with neurotmesis. Neurotmesis, according to Seddon's classification, is the most serious nerve injury in the scheme. In this type of injury, both the nerve fiber 14b and the nerve sheath are disrupted. While partial recovery may occur, complete recovery is not possible. Neurotmesis involves loss of continuity of the axon and the encapsulating connective tissue 14c, resulting in a complete loss of autonomic function, in the case of renal nerve fibers 14b. If the nerve fiber 14b has been completely divided, axonal regeneration causes a neuroma to form in the proximal stump.

A more stratified classification of neurotmesis nerve damage may be found by reference to the Sunderland System as is known in the art. The Sunderland System defines five degrees of nerve damage, the first two of which correspond closely with neurapraxia and axonotmesis of Seddon's classification. The latter three Sunderland System classifications describe different levels of neurotmesis nerve damage.

The first and second degrees of nerve injury in the Sunderland system are analogous to Seddon's neurapraxia and axonotmesis, respectively. Third degree nerve injury, according to the Sunderland System, involves disruption of the endoneurium, with the epineurium and perineurium remaining intact. Recovery may range from poor to complete depending on the degree of intrafascicular fibrosis. A fourth degree nerve injury involves interruption of all neural and supporting elements, with the epineurium remaining intact. The nerve is usually enlarged. Fifth degree nerve injury involves complete transection of the nerve fiber 14b with loss of continuity.

Figure 4:
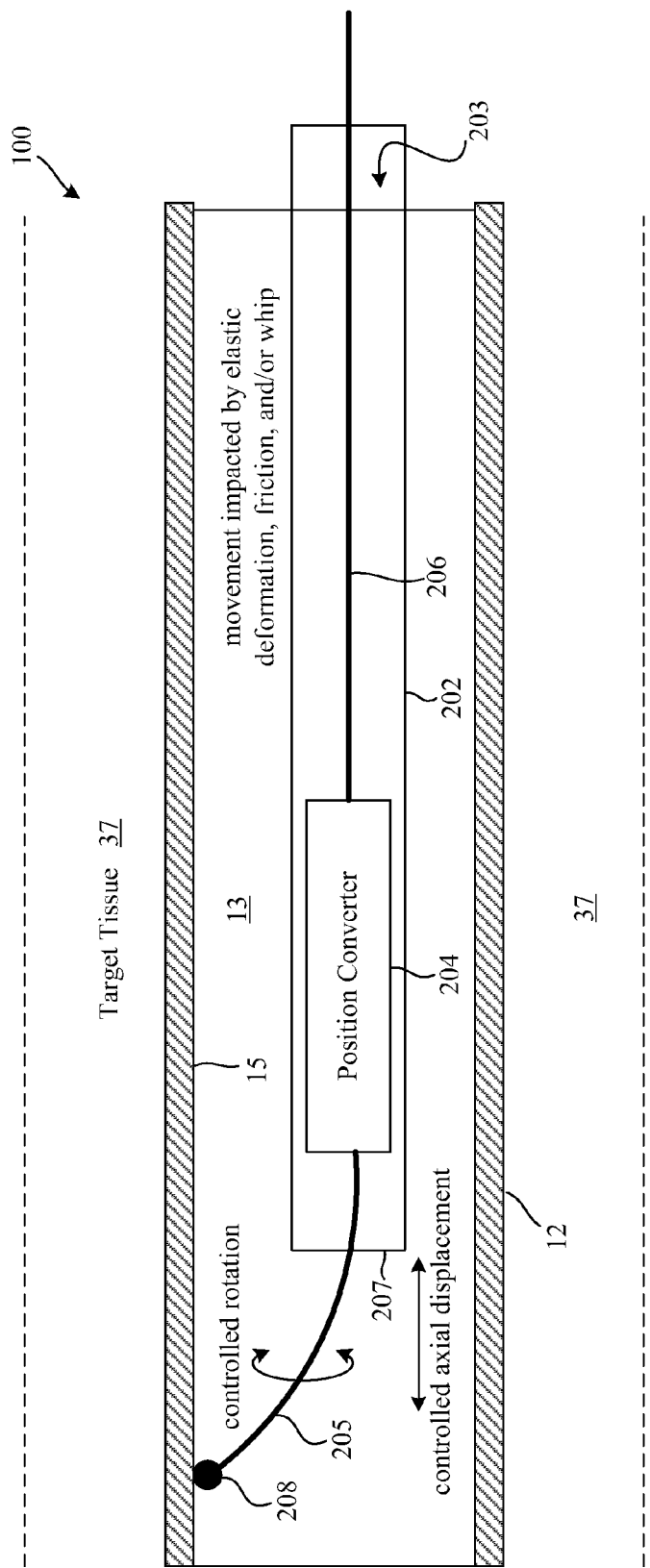
FIG. 4 illustrates an apparatus for ablating target tissue of a vessel which incorporates precision electrode movement control in accordance with various embodiments.

Referring now to FIG. 4, a distal end of an ablation catheter 100 is shown deployed in a renal artery 12 of a patient. According to this embodiment, the ablation catheter 100 includes a flexible shaft 202 and a lumen 203 that extends along the length of the shaft 202. The length of the shaft 202 is preferably sufficient to access a desired location of the body, such as the patient's renal artery 12 as shown in this illustrative example. A flexible actuation member 206 is provided within the lumen 203 of the shaft 202 and extends to the proximal end of the shaft 202. The actuation member 206 is movable within the lumen 203 of the shaft 202 and subject to one or more of elastic deformation, friction, and with along its length during movement within the shaft's lumen 203. The proximal end of the actuation member 206 may be fitted with a handle or other arrangement that facilitates rotational and axial movement of the actuation number 206 by a clinician or a robotic system.

The embodiment shown in FIG. 4 further includes a flexible support member 205 coupled to a distal end of the actuation member 206 and is configured to be extendable beyond the distal tip 207 of the shaft 202 and into a lumen 13 of the renal artery 12. An electrode 208 is provided at a distal end of the support member 205 and configured to contact a wall 15 of the renal artery 12 and deliver high-frequency AC energy sufficient to ablate perivascular renal nerve tissue 37 proximate the electrode 208. The support member 205 preferably has a curved shape configured to urge the electrode 208 into contact with the wall 15 of the renal artery 12. A position converter 204 is provided at the distal end of the shaft 202 and coupled to the distal end of the actuation member 206 and a proximal end of the support member 205.

The position converter 204 is configured to convert movement of the actuation member 206 into at least controlled rotational movement of the support member 205 and the electrode 208 to one of a plurality of stable circumferential positions substantially free of one or more of elastic deformation, friction, and whip impacting actuation member movement. The position converter 204 may also be configured to convert movement of the actuation member 206 into controlled axial movement of the support member 205 and the electrode 208 to one of a plurality of stable axial position. In some embodiments, the actuation member 206 and the support member 205 define a continuous member, and the position converter 204 acts upon this continuous member. In other embodiments, the actuation member 206 and the support member 205 define separate members, each having a proximal end and a distal end. In such embodiments, the proximal end of the support member 205 and the distal end of the actuation member 206 are coupled via the position converter 204.

Figure 5:
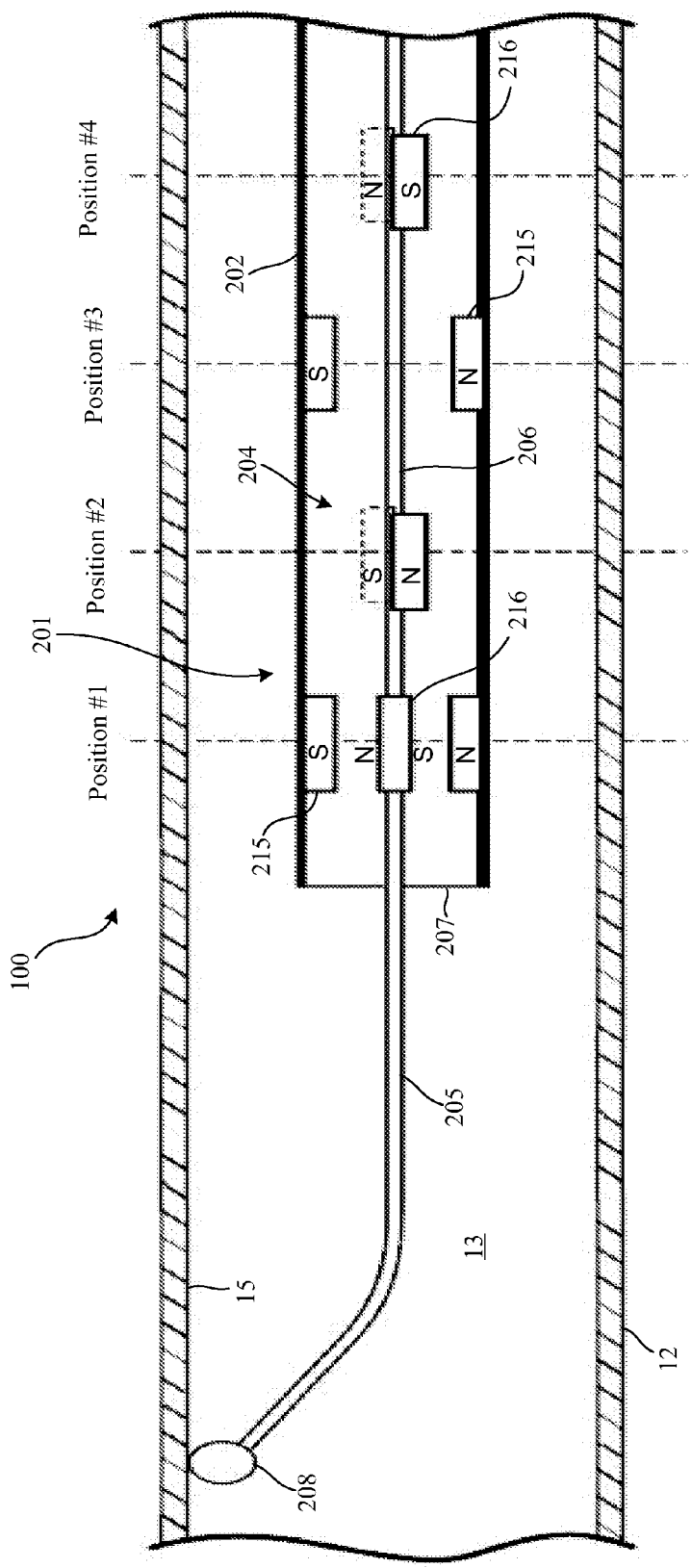
FIG. 5 illustrates an apparatus for ablating target tissue of a vessel which incorporates precision electrode movement control using a magnetic position converter in accordance with various embodiments.

Turning now to FIG. 5, there is illustrated a position converter 204 which includes a magnetic indexing arrangement 201 provided at a distal end of an ablation catheter 100 in accordance with various embodiments. The position converter 204 shown in FIG. 5 provides for magnetic alignment of the support member 205 and the electrode 208 using a discrete magnetically actuated indexing mechanism, so that the electrode 208 can be positioned at the appropriate locations along and around the wall 15 of the renal artery 12. The distal end of the support member 205 is typically curved, so that the electrode 208 makes good contact with the vessel wall 15. The magnetic indexing arrangement 201 is configured to magnetically urge the support member 205 and the electrode 208 to one of a plurality of stable circumferential positions. In some embodiments, a representative example of which is shown in FIG. 5, the magnetic indexing arrangement 204 is configured to magnetically urge the support member 205 and the electrode 208 to one of a plurality of stable circumferential and axial positions.

A magnet 216 is situated on the actuation member 206 at a desired location. Magnets 215 situated on the catheter's shaft 202 interact with the actuation member magnet 216 to urge the support member 205 and electrode 208 into only specific stable locations. The support member 205 and electrode 208 are advanced and rotated between the stable locations by the clinician or a robotic system. Advantageously, only rough imaging information is required to verify that the electrode 208 is in the desired location, since the magnetic forces prevent small misalignments, and the electrode 208 is stable only in a substantially different position which could easily be seen on an imaging device.

According to a representative method of use, the support number 205 and electrode 208 are advanced to the distal-most extent, at which point the electrode 208 is activated with the magnets 216, 215 aiding in circumferential alignment at a first treatment location. The support member 205 may be withdrawn a short distance into the catheter's shaft 202 and the electrode 208 activated again, with the magnets 216, 215 aiding in positioning the electrode 208 at a circumferential orientation different from the first location, and so forth until ablation has been performed at all desired treatment locations.

According to various embodiments, the shaft 202 of the ablation catheter 100 includes multiple sets of magnets 215 at different axial locations, with polarities arranged at different circumferential points at the different axial locations. In the embodiment illustrated in FIG. 5, for example, there are four axial positions indicated (axial positions #1, #2, #3, and #4) which are located 90° apart from one another. The polarity of each magnet of the shaft magnet arrangement 215 and that of the support member magnet arrangement 216 is indicated as N (North) or S (South).

Pairs of magnets 215 are situated circumferentially offset from one another by 90° at the four axial positions #1, #2, #3, and #4, each of which defines a magnetically stable position. A single magnet is shown situated on the support member 205. The support member 205 and electrode 208 are urged by the magnetic forces to orient at these axial positions to four different circumferential directions. For additional alignment force, the support member 205 can include multiple magnets 216 oriented appropriately so that the multiple sets of shaft magnets 215 and multiple support member magnets 216 interact.

When the support member 205 is advanced to one axial position, the magnets 215 on the shaft 202 interact with the magnet 216 on the support member 205 to urge the electrode 208 to one circumferential location. When the support number 205 is advanced or retracted to a different axial position, the magnets 215 on the shaft 202 interact with the magnet 216 on the support member 205 to urge the electrode 208 to a different circumferential location. In this way, a desired number (e.g., 2 to 10) discrete ablation sites, for example, can be obtained at predetermined axial and circumferential locations. Any one spot in the renal artery 12 would have minor or small areas of injury, and any subsequent healing response or stenosis would be insignificant.

It is understood that the number of magnet pairs and location of these pairs (circumferentially and/or axially) on the shaft 202 can differ from that shown in FIG. 5 to achieve a desired number of magnetically stable positions at desired circumferential and/or axial directions. For example, six magnetically stable positions can be achieved by situating a pair of magnets 205 on the shaft at desired spaced-apart axial positions circumferentially offset from one another by 60°. By way of further example, eight magnetically stable positions can be achieved by situating a pair of magnets 205 on the shaft at desired spaced-apart axial positions circumferentially offset from one another by 45°. In some embodiments, it may be desirable to provide controlled circumferential positioning of the support member 205 at a single axial location, such as for creating a circumferential lesion in target tissue. In such embodiments, pairs of magnets would be situated circumferentially offset from one another by 90° or other desired angle at a specified axial location of the shaft 202.

Figure 6:
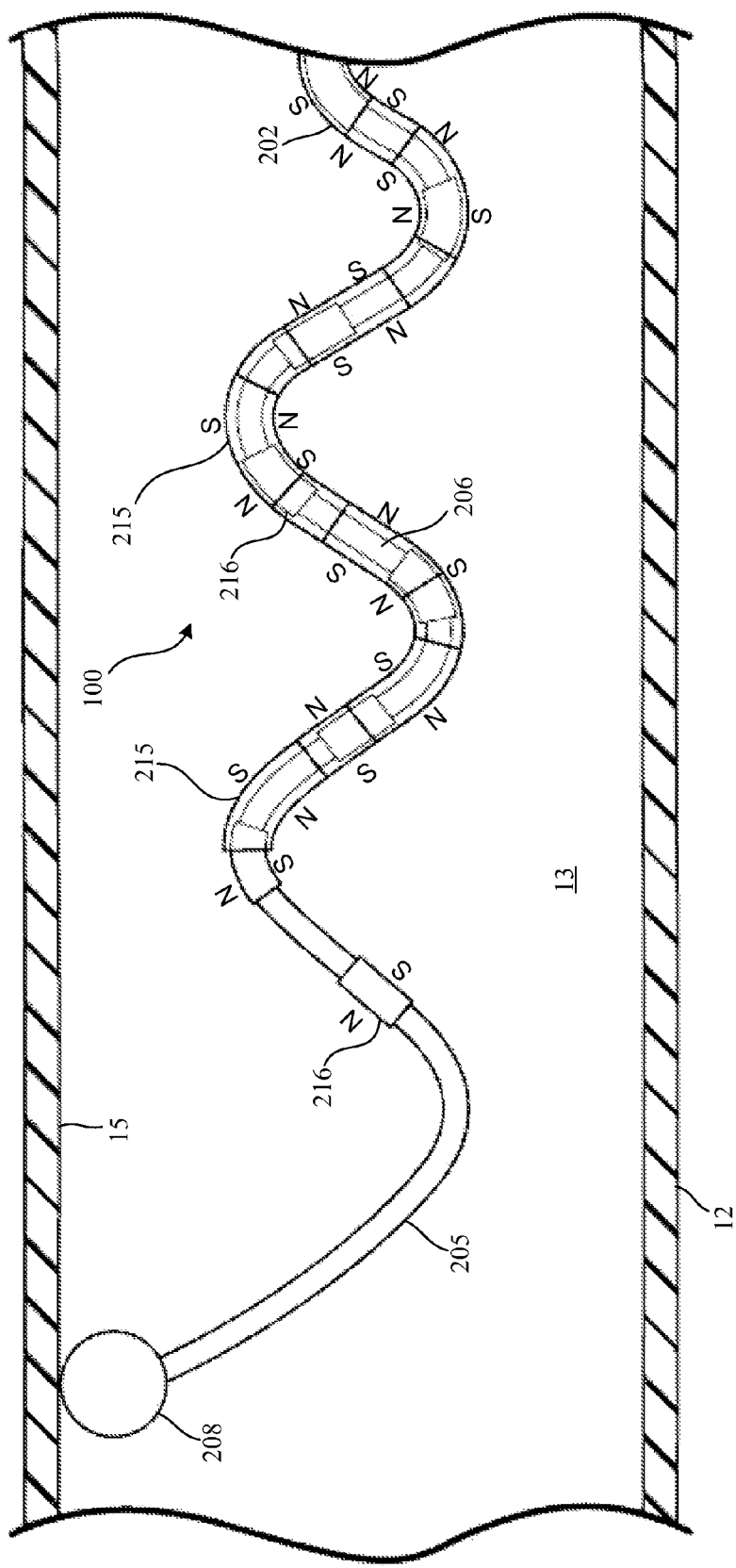
FIG. 6 illustrates an apparatus for ablating target tissue of a vessel which incorporates precision electrode movement control using a magnetic position converter arranged in a helical or spiral shape in accordance with various embodiments.

In accordance with other embodiments, and with reference to FIG. 6, a catheter, such as a guiding catheter, includes a magnetic indexing arrangement having a helical configuration, so that the support member 205 and electrode 208 are guided along a predictable helical path. The distal end of the shaft 202 is preferably fashioned to include a pre-form a helical shape. Additional magnetic or other alignment or indexing features can be incorporated to provide limited axial stability as well, so that a number of discrete ablation locations can be obtained, and spaced apart as desired.

The magnets 215 in the catheter's shaft 202 can be continuous, or a series of oriented magnets. The magnets on the support member 205 can similarly be continuous or a series of oriented magnets. According to some embodiments, when the support member 205 is advanced or retracted by corresponding movement of the actuation member 206, the support member 205 rotates in a predictable helical path, providing position control for the electrode 208 along a predictable helical path on the artery wall 15. In other embodiments, when the support member 205 is rotated by corresponding movement of the actuation member 206, the support member 205 rotates in a predictable circumferential path, providing position control for the electrode 208 along a predictable circumferential path on the artery wall 15. Intermittent application of RF energy to electrical conductors coupled to the electrode 208 produces a helical pattern or a circumferential pattern of separate ablation zones. In some embodiments, a physical helical groove can be provided to further aid in orienting the support member 205 and electrode 208 along a predictable helical path.

If alignment mechanisms were incorporated near the proximal hub of the ablation catheter as in the case of conventional approaches, curvature, poor torque transmission and/or friction could significantly reduce the effectiveness of such alignment mechanisms. Because the present embodiments use magnetic alignment forces that are applied near the distal end of the shaft 202 and actuation member 206, any elastic deformation in the bulk of the shaft 202 or actuation member 206 would have no significant effect on electrode 208 positioning (rotational and/or axial positioning).

Multiple magnets 215 around the circumference of the catheter's shaft 205 can be used to create multiple discrete stable locations of the support member 205 and electrode 208 at the same axial location, so that two or more small ablation spots can be obtained at that axial location, spaced circumferentially apart to control artery wall injury. An additional set of magnets 216 can be used to similarly guide the support member 205 and electrode 208 to two or more stable circumferential locations at a different axial location. In this way, less axial distance is required to obtain discrete areas of ablation, which may be an advantage in anatomies with short renal artery trunks. Mechanical guides near the end of a catheter's shaft 202 can be used to control the location or orientation of the electrode 208. Mechanical guides and magnetic guides can be used in combination.

In accordance with various embodiments, apparatuses and methods provide for circumferential position control of an RF electrode placed in vessel of the body using a ratcheting arrangement provided at a distal end of the shaft of an ablation catheter. An ablation catheter employing a ratcheting arrangement that provides for precision control of an electrode's circumferential position is particularly useful for ablating perivascular renal nerves adjacent the renal artery of the patient. To avoid renal artery stenosis, discrete zones of ablation can be created by moving an RF electrode axially and/or circumferentially in the renal artery.

According to various embodiments, a ratcheting position control arrangement includes a spring-loaded rotating ratcheting element, like portions of a ballpoint pen retraction mechanism. In a pen, for example, the ink reservoir typically does not rotate, but components of the ratcheting mechanism do. In some embodiments, the ratcheting position control arrangement can be actuated to move the ablation electrode to a number of discrete circumferential stable locations were ablation is performed. In such embodiments, each actuation of the ratcheting causes the ablation electrode to move from one stable circumferential location to the next stable circumferential location. This process is repeated until ablation has been performed at each of the stable circumferential locations.

In accordance with other embodiments, combined axial and circumferential positioning of the ablation electrode is achieved. In embodiments where the rotation feature of the ratchet mechanism is combined with the axial displacement feature (like the pen retracting), the ablation electrode is moved both axially and circumferentially between discrete stable positions. With each actuation of the ratchet mechanism, the electrode moves to a new stable position. At each stable position, RF energy is delivered by the ablation electrode to create a controlled region of injury. The combined effect of separate injury regions causes ablation of the perivascular renal nerves with beneficial effect on hypertension, with limited areas of renal artery injury. With this approach, a predetermined number of discrete ablation sites can be obtained at predetermined axial and circumferential locations. Any one spot in the renal artery would have minor or small areas of injury, and any subsequent healing response or stenosis would be insignificant.

Cooling can be incorporated into the ablation catheter design to further reduce renal artery injury. For example, the ablation catheter can be implemented as an infusion catheter, in which a biocompatible cooling fluid is transported from a proximal end of the catheter to the distal end of the catheter. Provision of cooling at the electrode-tissue interface can reduce the risk of thermal injury to the renal artery wall. Various other cooling approaches are contemplated.

In apparatuses of the present disclosure, the support member to which the ablation electrode is mounted can be coupled to the rotating ratcheting element so that it rotates 60 or 90 degrees (or other predetermined angles), for example, at each actuation of the ratchet mechanism. When the actuation member is pushed or pulled at its proximal and to overcome a spring force, a rotating ratchet mechanism is actuated which rotates the support member and electrode to the next stable circumferential position.

In other embodiments, combined axial and circumferential positioning is provided. In configurations where the rotation feature of the ratchet mechanism is combined with the axial displacement feature (like the pen retracting), the support member and electrode move both axially and circumferentially between discrete positions. Rather than pushing or pulling on the RF electrode wire to activate the ratchet mechanism, a separate control wire or tube can be provided.

Figure 7:
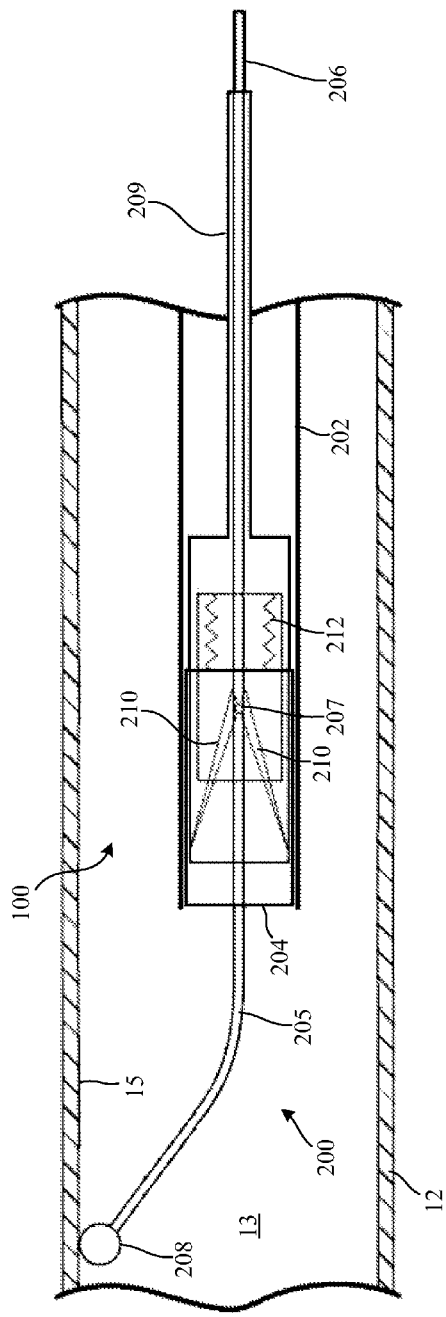
FIG. 7 illustrates an apparatus for ablating target tissue of a vessel which incorporates precision electrode movement control using a ratcheting position converter in accordance with various embodiments.
Figure 8:
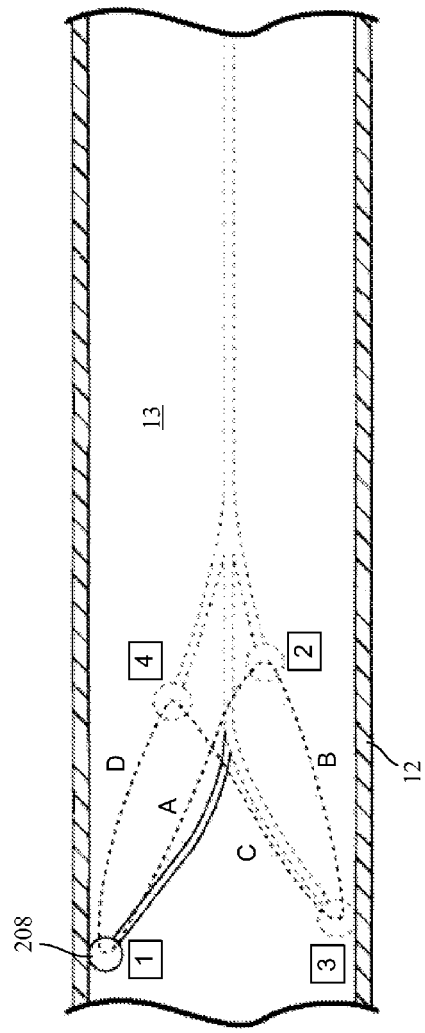
FIG. 8 illustrates an apparatus for ablating target tissue of a vessel which incorporates precision electrode movement control using a ratcheting position converter in accordance with other embodiments.

Referring now to FIGS. 7 and 8, there is shown a position converter implemented as a ratcheting arrangement 204 in accordance with various embodiments. The ratcheting arrangement 204 is provided at a distal end of the shaft 202 and has a proximal end and a distal end. A spring arrangement 212 is situated at the proximal end of the ratcheting arrangement 204. At the distal end of the ratcheting arrangement 204, a keyway arrangement 200 preferably includes a multiplicity of keyways 210. A keyway 210 defines a guide path that constrains the movement of the support member 205 and electrode 208 to a predetermined path, such as by limiting the rotational and/or axial travel of the support member 205 and electrode 208.

Typically, the ratcheting arrangement 204 incorporates a multiplicity of keyways 210, although a single keyway 210 may be appropriate in some applications. The keyways 210 are configured to receive a key component 207 provided on the distal end of the actuation member 206. Each of the keyways 210 has opposing end locations, each of which can define a predetermined stable circumferential and/or axial position for orienting the support member 205 and the electrode 208. A multiplicity of circumferentially spaced keyways 210 having an axial aspect may be incorporated in the ratcheting arrangement 204. Depending on the configuration of the ratcheting arrangement 204, a desired number of discrete ablation sites can be obtained, such as between two and eight discrete ablation sites, at predetermined axial and circumferential locations. Various additional components including gear or spring elements can be incorporated into the ratcheting arrangement 204 in accordance with various embodiments.

FIG. 7 further shows a control member 209 which can be used to actuate the ratcheting arrangement 204. The control member 209 can be implemented as a control wire or, as shown in FIG. 7, a control tube. In embodiments where the ratcheting arrangement 204 provides for rotational positioning of the support member 205 and electrode 208 with no axial positioning provided, the control member 209 need not be included, and an actuation member 206 of a type previously described herein can be used to actuate the ratcheting arrangement 204. In such embodiments, actuation of the ratcheting mechanism 204 can be accomplished by pushing and pulling the actuation member 206. In embodiments where the ratcheting arrangement 204 provides for both rotational and axial positioning of the support member 205 and electrode 208, the separate control member 209 may be employed in the actuation of the ratcheting arrangement 204.

FIG. 8 schematically illustrates the controlled movement of the ablation electrode 208 between four stable positions located circumferentially and axially apart from one another. The electrode 208 follows a generally zigzag path from one stable position to another resulting from actuation of the ratcheting mechanism 204 and constrained movement dictated by the keyways 210. When the electrode 208 reaches each of the stable positions, the support member 205 has a spring bias that forces the electrode 208 against the wall 15 of the renal artery 12. Depending on the keyway design, the electrode 208 may or may not maintain continuous contact with the renal artery wall 15 when traversing a path between stable positions.

The ablation procedure preferably begins by advancing the support member 205 and electrode 208 to its distal-most position, which is shown as stable position #1 in FIG. 8. In general, the support member 205 and electrode 208 are moved from one stable position to the next stable position in response to each actuation of the ratcheting arrangement 204, which in this illustrative embodiment is accomplished using the control member 209. With the electrode 208 located at stable position #1, RF energy is delivered to the electrode 208. After completing ablation at stable position #1, the control member 209 is pushed, causing the support member 205 and electrode 208 to traverse along path-A. The control member 209 is pushed until a spring force produced by the spring arrangement 212 is overcome, at which point the electrode 208 is located at stable position #2. RF energy is delivered to the electrode 208 at stable position #2 until ablation at this location is completed. Pushing the control member 209 causes the electrode 208 to move from stable position #2 to stable position #3 along path-B. RF energy is delivered to the electrode 208 at stable position #3 until ablation at this location is completed. The control member 209 is again pushed by the clinician or robotic system causing the electrode 208 to move from stable position #3 to stable position #4 along path-C. RF energy is delivered to the electrode 208 at stable position #4 until ablation at this location is completed. The electrode 208 can be moved to its initial starting location at stable position #1 by again pushing the control member 209, causing the electrode 208 to move from stable position #3 to stable position #4 along path-D. After completing ablation at all stable locations, the support member 205 electrode 208 can be retracted into the lumen of the shaft 202.

Figure 9:
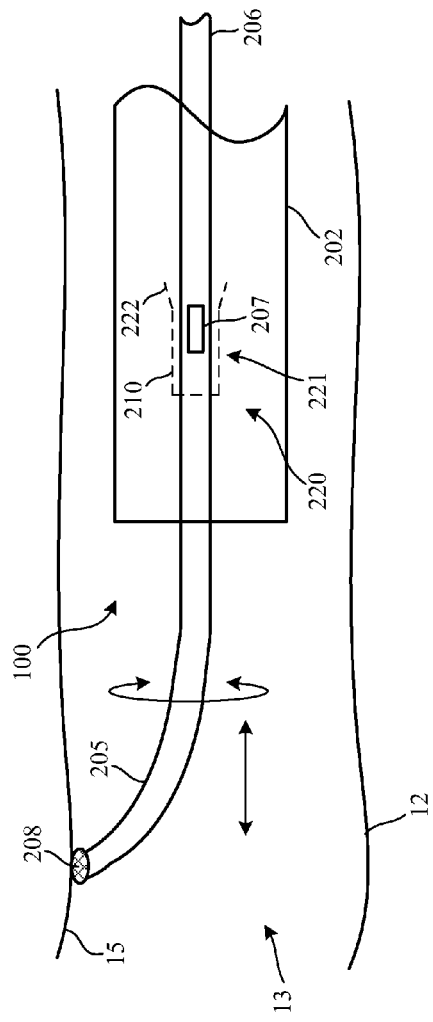
FIG. 9 illustrates an apparatus for ablating target tissue of a vessel which incorporates precision electrode movement control using a geometric orientation position converter in accordance with other embodiments.
Figure 10:
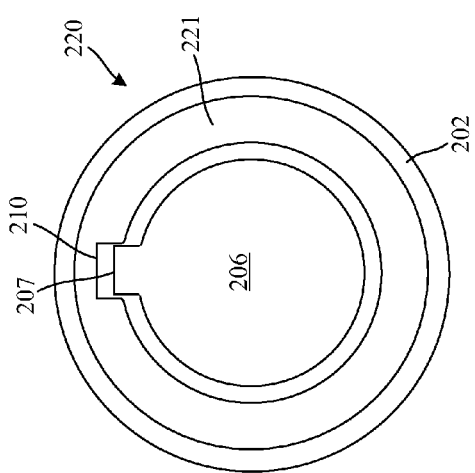
FIG. 10 shows the a cross-section of a geometric orientation position converter of a type shown in FIG. 9.
Figure 11:
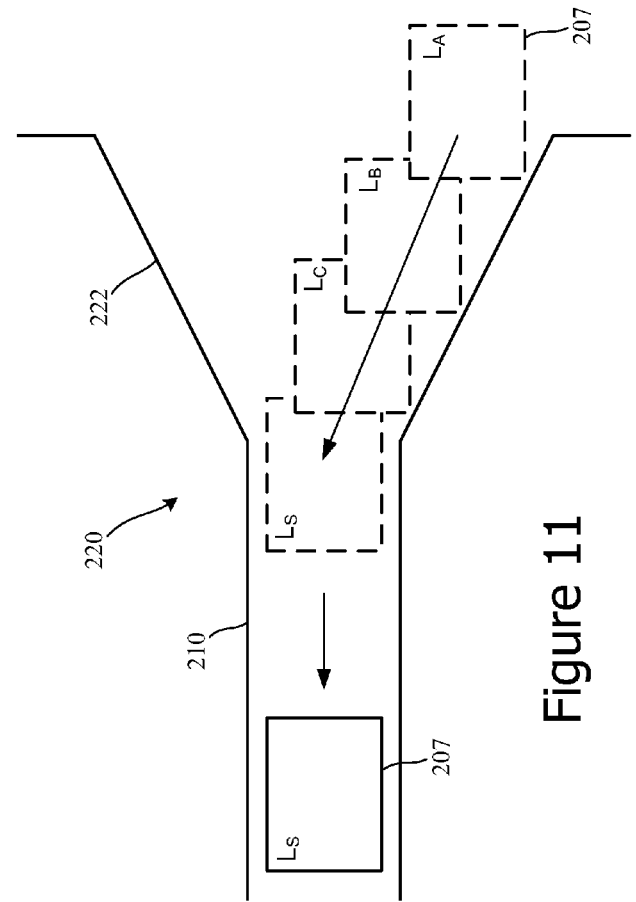
FIG. 11 shows a tapered entrance to a keyway structure of a geometric orientation position converter of a type shown in FIG. 9.
Figure 12A:
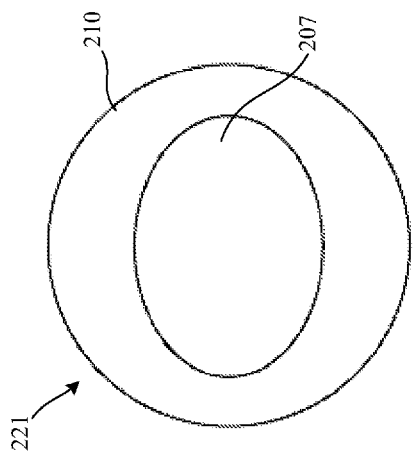
FIGS. 12A-12D show various sectional views of a keyway and key component having various geometries in accordance with various embodiments.
Figure 12B:
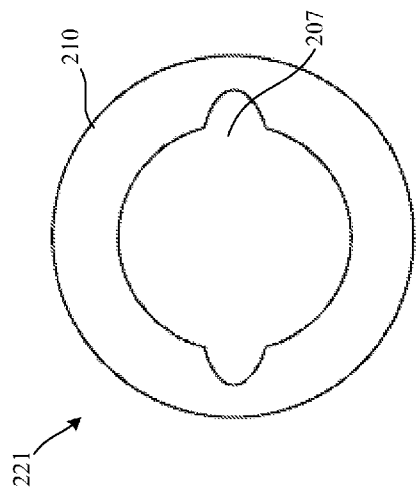
Figure 12C:
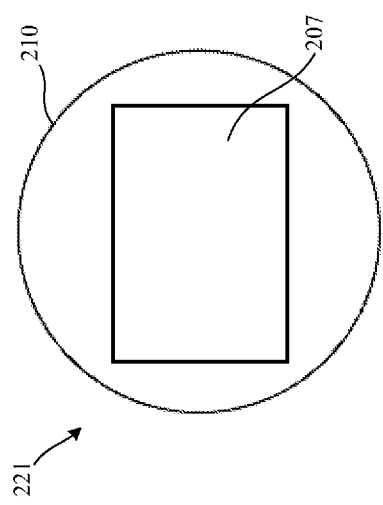
Figure 12D:
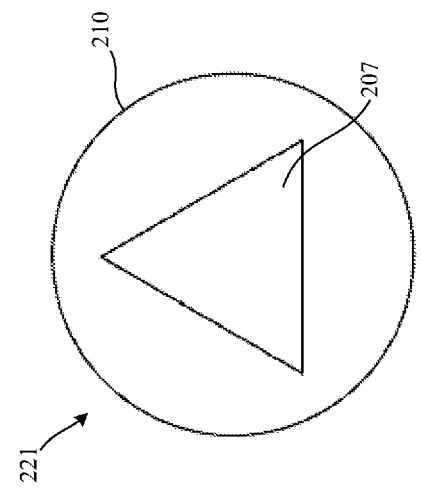

According to various embodiments, and with reference to FIGS. 9-11, a position converter of an ablation catheter 100 includes a geometric keyed orientation mechanism 220 provided at the distal end of a guiding catheter or sheath, and further includes corresponding key components 207 provided on the actuation member 206. The geometric keyed orientation mechanism 220 is configured to guide a key component 207 of the actuation member 206 into and along a keyway arrangement 221 that limits movement of the support member 205 and the electrode 208 to one of a plurality of stable circumferential positions. In some embodiments, the geometric keyed orientation mechanism 220 is configured to guide a key component 207 of the actuation member 206 and the electrode 208 to one of a plurality of stable circumferential positions and one of a plurality of stable axial position.

The keyway arrangement 221 includes a multiplicity of axial space-apart keyways 210 each comprising a tapered entrance 222 configured to guide the key component 208 into alignment with each of the keyways 210. The tapered entrance 222 of each keyway 210 can be configured to guide the key component 208 into the keyway 210 if the relative orientation is within +/−45, 60 or 90 degrees (or some other angle range), for example. FIG. 11 illustrates that only a rough orientation of the actuation member 206 needs to be transmitted from the proximal end of the actuation member 206 to the geometric keyed orientation mechanism 220, since the tapered entrance 222 provides for fine orientation adjustments of the support member 205 and electrode 208. For example, FIG. 11 shows misalignment between a key component 207 of the actuation member 206 and a keyway 210 which provides a desired electrode orientation. Gross misalignment between the key component 207 and the keyway 210 is corrected by the tapered entrance 222, which channels the misaligned key component 207 into proper alignment with the keyway 210.

In some embodiments, the keyway arrangement 221 includes a multiplicity of space-apart keyways 210, with alternate keyways 210 of the keyway arrangement 221 having differing lengths. In other embodiments, the keyway arrangement 221 includes a multiplicity of circumferentially and axially spaced-apart keyways 210. The keyways arrangement 221 may be formed with keyways 210 having varying geometries. For example, as with reference to FIGS. 12A-12D, keyways 210 may have one of an elliptical, square, rectangular, triangular, or other geometric cross-section that provides stability to properly orient the support member 205 and electrode 208.

In some embodiments, and with reference to FIGS. 13A-14C, a helical keyway or a zigzag keyway can be used, with the clinician providing slight bias or rough orientation to move the actuation member 206 to the next desired location, and the refined orientation is provided by the keyway/keyway component geometry. A keyway transition feature, such as a short axial slot 212, can be incorporated into a keyway arrangement 221 to provide tactile feedback indicating a transition from one keyway 210 to the next keyway 210.

In some configurations, pushing or pulling on the actuation member 206 relative to the guiding catheter or sheath 202 moves the keyed components between the stable locations. FIGS. 13A-14C schematically illustrates various configurations of keyways 210. In FIGS. 13A-14C, the generally cylindrical keyway configurations have been opened up for ease of illustration. In addition to the configurations illustrated in FIGS. 13A-14C, helical patterns, or combinations of various patterns can be used to control electrode positions to a set of limited-stability locations.

Maintaining good contact with the artery wall during ablation of perivascular renal nerves for hypertension control has been difficult. If contact is variable, the tissue temperatures are not well controlled, and an ablative temperature may not be achieved in the target tissue, while temperature in other areas, such as portions of the artery wall, may deviate enough to cause unwanted arterial tissue injury. For ideal anatomy, good vessel apposition can be achieved more easily. However, especially with tortuous or diseased renal arteries, there can be very poor contact to effectively and predictably transfer heat, electrical current, or other energy from an ablation device to the tissue. Conventional RF electrode wires have not provided the required balance of pushability, torque control, and flexibility along the length to provide for reliable contact of the electrode with the vessel wall.

Figure 15:
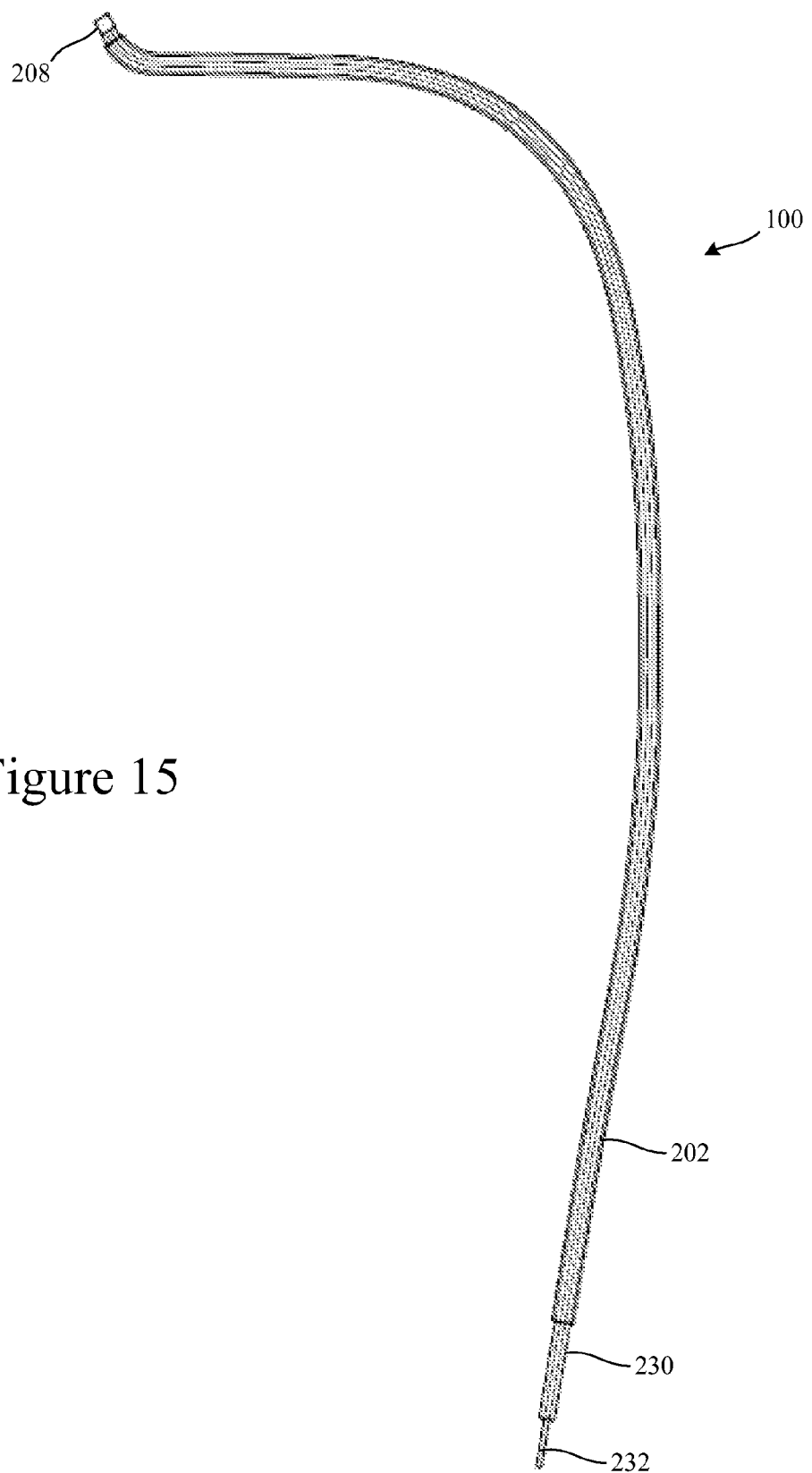
FIG. 15 illustrates an ablation catheter which incorporates an elongated metallic slotted tube in accordance with various embodiments.

Apparatuses and methods of the disclosure provide for improved directability of intra-arterial RF electrode wires for better apposition to the artery wall during renal nerve ablation. According to various embodiments, and with reference to FIG. 15, and ablation catheter 100 includes a flexible shaft 202 having a lumen dimensioned to receive an RF electrode wire in the form of a slotted tube structure 230. In embodiments involving renal denervation, the shaft 202 has a proximal end, a distal end, a length, and a lumen extending between the proximal and distal ends. The length of the shaft 202 is sufficient to access a patient's renal artery relative to a percutaneous access location. The slotted tube 230 has a proximal end, a distal end, and a length extending between the proximal and distal ends sufficient to access the patient's renal artery relative to the percutaneous access location. The slotted tube 230 is dimensioned for displacement within the lumen of the shaft 202.

The slotted tube 230, according to various embodiments, comprises a multiplicity of regions defined along its length. Each of the slotted tube regions has disparate slot patterns associated with disparate mechanical properties, such as torque transmission and bending flexibility. An electrical conductor arrangement 232 extends along the length of the slotted tube 230. An electrode arrangement 208 is provided at a distal end of the slotted tube 230 and is coupled to the conductor arrangement 232. Electrode arrangement 208 is configured to deliver high-frequency AC energy sufficient to ablate perivascular renal nerve tissue proximate the renal artery.

According to various ablation methods, a guiding catheter or sheath 100 is directed to a renal artery and placed at a desired location and orientation within the artery. The slotted tube 230 is advanced within the lumen of the shaft 202 of the guiding catheter and positioned in contact with the renal artery wall at the treatment location. The RF electrode 208 is energized to cause ablation of perivascular renal nerves. After completing ablation at this site, the guiding catheter or sheath 100 is moved to another location within the renal artery, and the RF electrode 208 is energized to cause ablation of perivascular renal nerves adjacent this site. This process is repeated for the current renal artery and then the contra-lateral renal artery until all desired renal artery sites have been subject to ablation. The ablation catheter arrangement is that removed from the patient's body.

Figure 16:
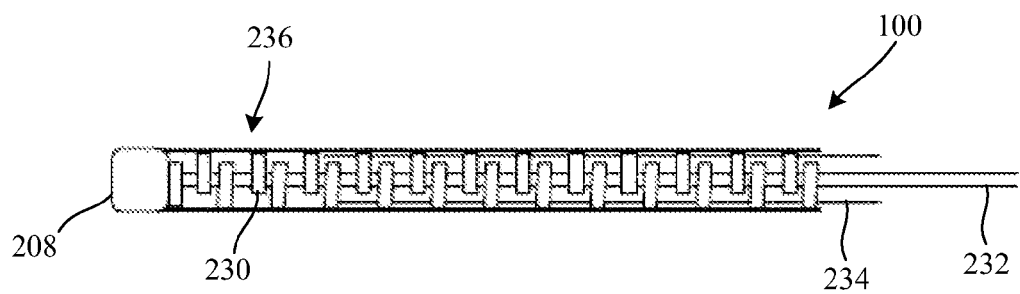
FIG. 16 shows various details of an elongated metallic slotted tube for use in an ablation catheter in accordance with various embodiments.

FIG. 16 shows various features of a slotted tube 230 in accordance with various embodiments. According to some embodiments, the slotted tube 230 is formed to include a metallic slotted tube shaft. In other embodiments, the slotted tube 230 is formed from material other than metal. For example, the slotted tube 230 may be constructed as a slotted polymer tube. In other configurations, the slotted tube 230 may incorporate ringed, helical, or braided components. In some configurations, fiber-reinforced components may be used to construct the slotted tube 230. Also, separate components for each segment of the slotted tube 230 may be bonded together, for example. The slotted tube configuration provides superior torque control for accurate positioning and orientation of the electrode, while maintaining sufficient flexibility to facilitate access to the target site.

As is shown in FIG. 16, an RF electrode 208 is attached at the distal tip of the slotted tube 230. Insulated electrical conductor wires 232 pass through the central lumen of the slotted to 230 and provide power to the RF electrode 208. The proximal ends of the electrical conductor wires 232 connect to an external power supply and control unit.

In some embodiments, the slotted to 230 is lined with a thin polymeric tube 234 that surrounds the slotted tube 230 other than at one or more perfusion locations at the distal end of the slotted tube 230. For example, short portions of the slotted tube 230 near the distal end may be purposefully devoid of the polymeric tube 234. Alternatively, the polymeric tube 230 can extend as far as the electrode 208, and include perforations or apertures to define a perfusion region. The polymeric tube 234 forms a fluid-type lumen around the slotted tube 230 through which a liquid can be transported between the proximal and distal ends of the slotted to 230. For example, a cooling fluid may be transported from a fluid source at the proximal end of the slotted to 230 and transported to the distal perfusion region of the slotted tube 230 proximate the electrode 208. A biocompatible cooling fluid may be used to provide cooling at the electrode-tissue interface. The fluid-tight lumen surrounding the slotted tube 230 may also be used for flushing without leakage through the slots in the tube 230.

In some configurations, the slotted tube 230 is used to conduct electric current to a unipolar electrode 208, with the return path to a remote pad in contact with the patient's skin. In other configurations, the slotted tube 230 includes multiple electrodes 208 situated near the distal end, with insulated electrical conductor wires used to power the multiple electrodes. In still other configurations, one or more bipolar RF electrode pairs may be situated at the distal end of the slotted tube 230, with insulated electrical conductor wires as required.

One or more sensors near the distal end, such as temperature sensors, can be included, with insulated electrical conductor wires used for power or signal transfer for the sensors. For example, a temperature sensor may be situated at or near the electrode 208. The temperature sensor provides sensing of a temperature at the electrode-tissue interface during ablation. Signals generated by the temperature sensor can be transmitted to the distal end of the catheter 100 using conductor wires that extend through the slotted tube 230. Temperature signals can be used by an external power and control system to automatically or semi-automatically control power delivery (and cooling fluid if desired) to the electrode 208 during an ablation procedure.

Figure 17:
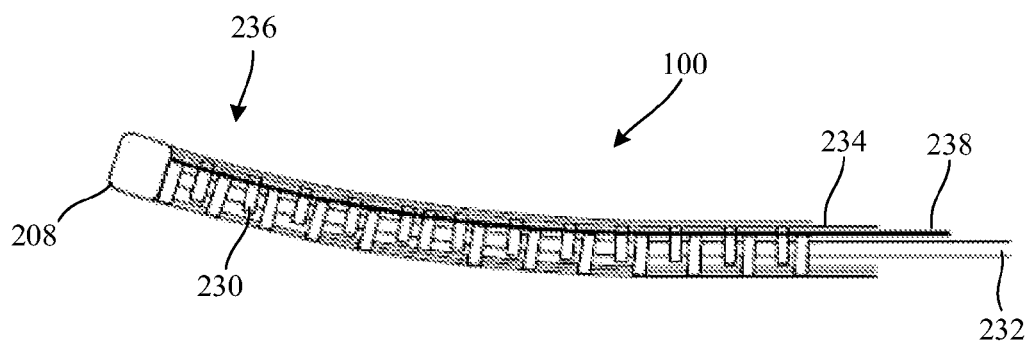
FIG. 17 shows various details of an elongated metallic slotted tube which incorporates a tension wire for controlling curvature of the slotted tube's distal tip.

FIG. 17 illustrates a slotted tube 230 with an active curve mechanism in accordance with various embodiments. The illustrative example shown in FIG. 17 includes a tension wire 238 coupled to the distal tip of the slotted tube 230 and extending between the distal tip and the proximal end of the slotted tube 230. The tension wire 238 causes the distal tip of the slotted tube 232 to curve in response to a tensioning force applied to the proximal end of the tension wire 238.

The slot pattern of the slotted tube 230 can be configured to obtain desired mechanical properties. For example, the slot pattern can vary, to provide tuned properties in different regions, and with transition zones to avoid abrupt property changes which could result in kinking or other problems. In general, the entire length of the slotted tube 230 is typically configured for good torque transmission so that the clinician can control the circumferential orientation of the electrode 208, with a moderate amount of bending flexibility to allow advancement through sheaths and the vasculature. In a tip region of the slotted tube 230, a short region of increased bending stiffness can be incorporated so that a tip curve is maintained to aid in directing the electrode 208 to contact the artery wall. The tip curve can be maintained by spring-like elasticity in this region. In an intermediate region of the slotted tube 230 near the tip region, enhanced bending stiffness can be incorporated so that the slotted tube 230 can easily bend at the renal artery ostium to minimize arterial trauma, even though the tip curve is maintained, and the enhanced torque transmission is used to control electrode orientation within the renal artery.

To further control mechanical properties at the tip region, the slot pattern of the slotted tube 230 can be tuned to provide a biased flexibility, such as to allow the tip curve to bend the electrode 208 outwardly towards the vessel wall in one plane, but to resist bending in an orthogonal plane, so that the circumferential positioning of the electrode 208 is well controlled. In some embodiments, a curve portion near the distal end of the slotted tube 230 can have a different slotted tube structure, or no slots, and provides an orientation curve so that the electrode 208 can be pressed towards the artery wall. The curved tip can have a preset curved shape which is maintained by forming or treating this region to a permanent curve, or a shape-memory material can be used to achieve the curve using thermal or other control. Alternatively, an active-curve mechanism can be provided, such as by using a biased tube structure and a tension wire 238 to actively flex the curve portion when desired. Other mechanisms can be used to control the curved tip portion, such as torsional bias, external sheath constraint, and a push-wire, for example.

A distinctive aspect of a slotted tube 230 in accordance with various embodiments is that its construction effectively decouples flexural and torsional stiffness of this structure. This provides for the "tuning" (e.g., optimizing or customization) of various mechanical properties of the slotted tube 230 at different axial locations along its length. Moreover, flexural stiffness can be non-linear due to interference between adjacent ribs of the slotted tube 230. The slotted tube 230 can be customized to incorporate different slot patterns at different axial locations along its length to achieve desired mechanical properties that may have at least some of the following attributes:

Single Plane Symmetry (slotted tube flexing in a preferred direction): This attribute imparts a directional steering capability, which can be achieved by providing longitudinally continuous spines within the slotted tube structure. If the spines are off-set from the axis, the shaft of the slotted tube 230 will have a preferred direction within the symmetry plane.

Multiple Symmetry Plane: If more than 2 axial spines are present, there will be multiple symmetry planes. The effect will be most pronounced with the presence of an even number of spines. This is a form of geometric keying.

Axisymmetric Flexibility: Adjacent connectors can be staggered so that axially uniform flexibility is provided with minimal loss of torsional rigidity. This may be viewed as a "flex coupler" design. If connecting spines precess or spiral along the axis, the shaft of the slotted tube 230 will tend to deform in a similar manner.

The preferred distribution of properties along the slotted tube 230 is typically dependent on the desired electrode configuration. Consider an electrode of a slotted tube 230 arranged tangent to the surface with an S-curve. The portion of the slotted tube 230 with the S-curve may have the following attributes:

a primary curve (closest to tip) having highly flexible axisymmetric flexure.

a pull wire terminates between the primary and a secondary curve.

the secondary curve having single plane symmetry to provide directional steering and stability.

a tertiary curve which is axisymmetric with moderate flexure to provide torque transmission and smooth axial control.

It is noted that for acute tip contact angles, the primary curve can be eliminated. Also, multi-plane symmetry in the tertiary curve provides a rotary detent effect. The effect is exaggerated if bending is concentrated in a short section of the slotted tube 230.

In accordance with an associated method, the slotted tube 230 can be guided to a treatment location in a renal artery using a guiding catheter or sheath, utilizing the enhanced torque control of the slotted tube 230 to orient the electrode 208 to a desired position in good contact with the artery wall. With the electrode 208 positioned against the artery wall at a desired site, RF energy is used to ablate perivascular renal nerves. An external control unit is used to energize the electrode 208, which can be configured for operation in either a unipolar mode (using an external pad return electrode) or a bipolar mode.

Figure 18:
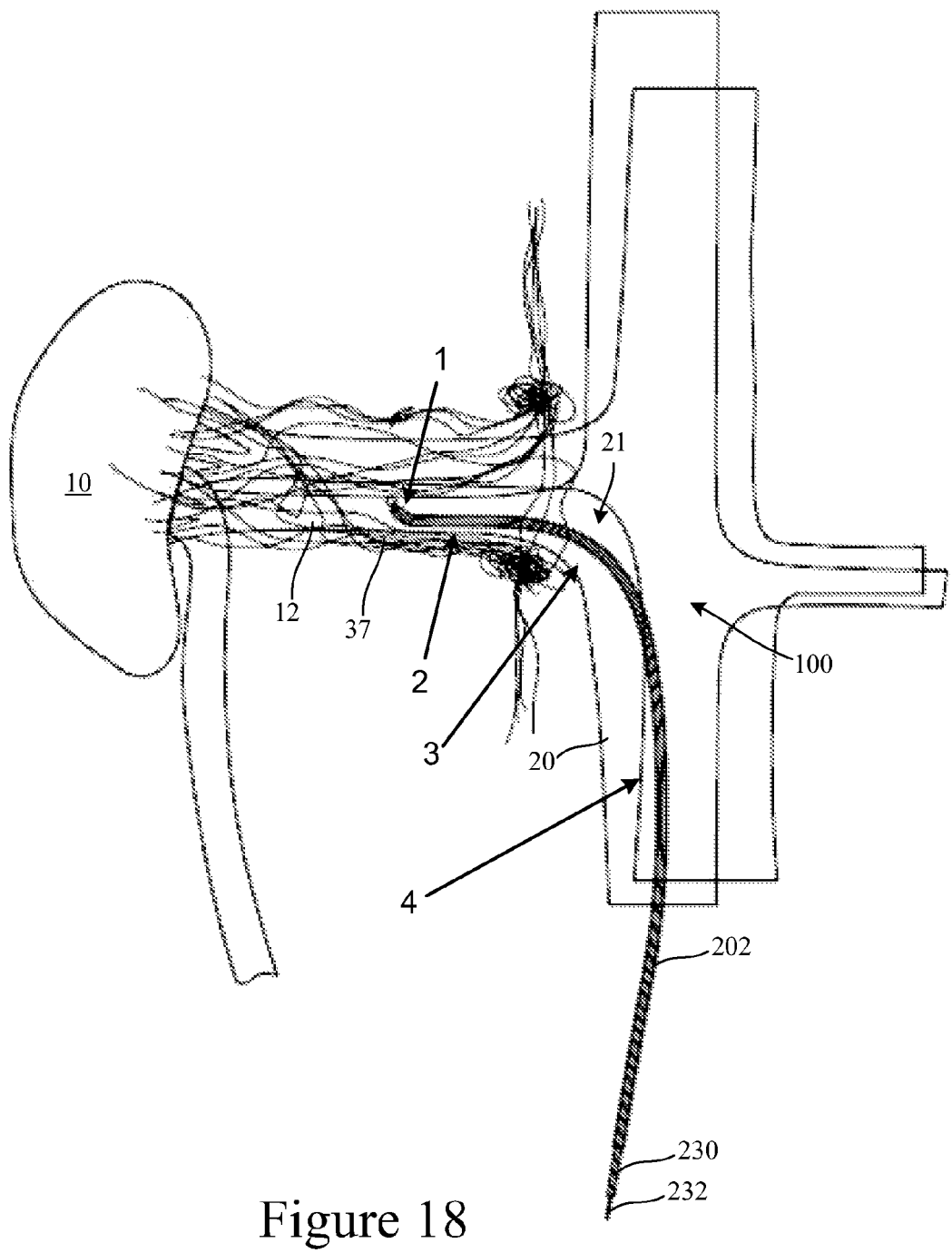
FIG. 18 illustrates an ablation catheter which incorporates an elongated metallic slotted tube deployed within a patient's renal artery for ablating perivascular renal nerve tissue in accordance with various embodiments.

In accordance with various embodiments, and with reference to FIG. 18, the slotted tube 230 is dimensioned for displacement within the lumen of the shaft of a guiding catheter or sheath, and includes a plurality of regions defined along its length having disparate slot patterns associated with disparate mechanical properties including torque transmission and bending flexibility. The multiplicity of regions defined along the length of the slotted tube 230 include a proximal region (4), a turn region (3), and a tip region (1). The proximal region (4) is defined between the proximal end of the slotted tube 230 and the turn region (3). The proximal region (4) preferably has a slot pattern configured to provide enhanced torque transmission relative to bending flexibility.

The turn region (3) preferably has a slot pattern configured to provide enhanced bending flexibility relative to torque transmission to facilitate bending of the slotted tube 230 around an aortorenal junction 21 at the ostium of the renal artery 12. The tip region (1) is defined between a distal tip of the slotted tube 230 and the turn region (3). The tip region (1) is configured to support the electrode(s) 208 and preferably has a curved shape. The tip region (1) preferably has a slot pattern configured to provide enhanced bending stiffness sufficient to maintain contact between the electrode(s) 208 and the wall 15 of the renal artery 12. In some embodiments, the multiplicity of regions defined along the length of the slotted tube 230 further includes an intermediate region (2) defined between the tip region (1) and the turn region (3). The slot pattern in the intermediate region (2) is preferably configured to provide a balance between torque transmission and bending flexibility. Not shown are transition regions between each of the distinct regions (1)-(4), which provide for a gradual change in slotted tube properties between regions.

Figure 19:
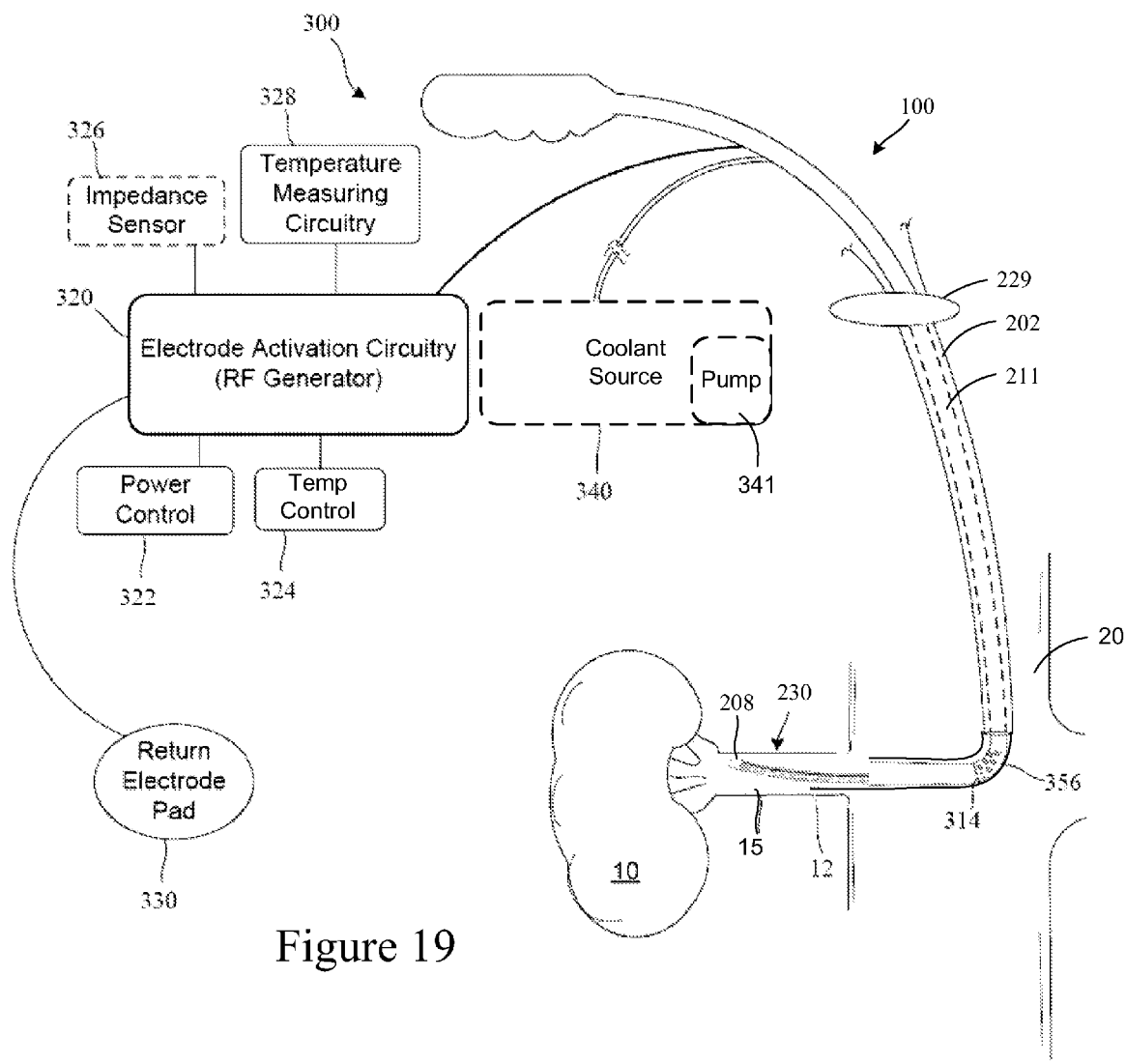
FIG. 19 shows a representative high frequency AC renal therapy apparatus in accordance with various embodiments.

FIG. 19 shows a representative RF renal therapy apparatus 300 in accordance with various embodiments of the disclosure. The apparatus 300 illustrated in FIG. 19 includes external electrode activation circuitry 320 which comprises power control circuitry 322 and timing control circuitry 324. The external electrode activation circuitry 320, which includes an RF generator, is coupled to temperature measuring circuitry 328 and may be coupled to an optional impedance sensor 326. The catheter 100, which can be configured as a guiding catheter, includes a shaft 202 that incorporates a lumen arrangement 211 configured for receiving an RF ablation wire configured as a slotted tube 230 and, if desired, a variety of other components, such as conductors, pharmacological agents, actuator elements, obturators, sensors, or other components as needed or desired. The catheter 100 is typically introduced into the arterial or venous system via a percutaneous access location 229.

The RF generator of the external electrode activation circuitry 320 may include a return pad electrode 330 that is configured to comfortably engage the patient's back or other portion of the body near the kidneys. Radiofrequency energy produced by the RF generator is coupled to the electrode 208 of the slotted tube 230 by conductor wires that extend between the electrode 208 and the proximal end of the catheter 100.

Renal denervation therapy using the apparatus shown in FIG. 19 is typically performed using the RF electrode 208 positioned at desired locations within the renal artery 12 and the return pad electrode 330 positioned on the patient's back, with the RF generator operating in a unipolar mode. In other implementations, two or more RF electrodes 208 can be situated at the distal end of the slotted tube 230 and configured for operation in a bipolar configuration, in which case the return electrode pad 330 is not needed. The radiofrequency energy flows through the electrode(s) 208 in accordance with a predetermined activation sequence (e.g., sequential or concurrent) and ablates target tissue which includes perivascular renal nerves.

In general, when renal artery tissue temperatures rise above about 113° F. (50° C.), protein is permanently damaged (including those of renal nerve fibers). If heated over about 65° C., collagen denatures and tissue shrinks. If heated over about 65° C. and up to 100° C., cell walls break and oil separates from water. Above about 100° C., tissue desiccates. According to some embodiments, the electrode activation circuitry 320 is configured to control activation and deactivation of the electrode(s) 208 in accordance with a predetermined energy delivery protocol and in response to signals received from temperature measuring circuitry 328. The electrode activation circuitry 320 preferably controls radiofrequency energy delivered to the electrode(s) 208 so as to maintain the current densities at a level sufficient to cause heating of the target tissue to at least a temperature of 55° C.

One or more temperature sensors situated at the distal end of the slotted tube 230 provide for continuous monitoring of renal artery tissue temperatures, and RF generator power is automatically adjusted so that the target temperatures are achieved and maintained. An impedance sensor arrangement 326 may be used to measure and monitor electrical impedance during RF denervation therapy, and the power and timing of the RF generator 320 may be moderated based on the impedance measurements or a combination of impedance and temperature measurements.

Marker bands 314 can be placed on one or multiple parts of the slotted tube 230 and the catheter's shaft 202 to enable visualization during the procedure. Other portions of the catheter's shaft 202, such as a hinge mechanism 356, may include a marker band 314. The marker bands 314 may be solid or split bands of platinum or other radiopaque metal, for example. Radiopaque materials are understood to be materials capable of producing a relatively bright image on a fluoroscopy screen or another imaging technique during a medical procedure. This relatively bright image aids the user in determining specific portions of the catheter 100 and slotted tube 230, such as the electrode 208, for example.

Various aspects of the disclosure embodiments can be applied to other directed energy mechanisms for renal nerve ablation, such as for directing laser or microwave or ultrasound or cryothermal energy or ionizing radiation to selected locations within the renal artery. "Back-up" support curves can be provided, akin to coronary guiding catheter curves, to use the opposite wall of the renal artery for additional support to ensure adequate contact between the electrode and the artery wall. These and other features disclosed in the following commonly owned patents and published applications can be selectively incorporated into the various embodiments disclosed herein:

U.S. Patent Publication No. 2011-0257523, filed as U.S. patent application Ser. No. 13/086,116 on Apr. 13, 2011, which claims the benefit of U.S. Provisional Patent Application Ser. No. 61/324,164 filed Apr. 14, 2010; U.S. Patent Publication No. 2011-0257641, filed as U.S. patent application Ser. No. 13/086,121 on Apr. 13, 2011, which claims the benefit of U.S. Provisional Patent Application Ser. No. 61/324,163 filed Apr. 14, 2010; U.S. Patent Publication No. 2012-0029496, filed as U.S. patent application Ser. No. 13/193,437 on Jul. 28, 2011, which claims the benefit of U.S. Provisional Patent Application Ser. No. 61/369,460 filed Jul. 30, 2010; U.S. Patent Publication No. 2011-0270238, filed as U.S. patent application Ser. No. 12/980,952 on Dec. 29, 2010, which claims the benefit of U.S. Provisional Patent Application Ser. No. 61/291,476 filed Dec. 31, 2009; U.S. Patent Publication No. 2011-0263921, filed as U.S. patent application Ser. No. 12/980,972 on Dec. 29, 2010, which claims the benefit of U.S. Provisional Patent Application Ser. No. 61/291,480 filed Dec. 31, 2009; U.S. Patent Publication No. 2011-0307034, filed as U.S. patent application Ser. No. 13/157,844 on Jun. 10, 2011, which claims the benefit of U.S. Provisional Patent Application Ser. No. 61/353,853 filed Jun. 11, 2010; and U.S. Patent Publication No. 2011-0264086, filed as U.S. patent application Ser. No. 13/087,163 on Oct. 14, 2011, which claims the benefit of U.S. Provisional Patent Application Ser. No. 61/324,165 filed Apr. 14, 2010, each of which is incorporated herein by reference.

Although many of the embodiments disclosed herein are directed to ablation of body tissue, it is to be understood that various embodiments are directed to control mechanisms situated at a distal end of an elongated flexible member that provide for precision movement of a component coupled to a distal end or other portion of the control mechanism, where the component need not include an ablation device. Embodiments of the disclosure are also directed to control mechanisms situated at a distal end of an elongated flexible member dimensioned for deployment within a vessel of the body that provide for precision movement of a component coupled to a distal end or other portion of the control mechanism. It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. An apparatus, comprising:
a catheter comprising a flexible shaft having a proximal end, a distal end, a length, and a lumen extending between the proximal and distal ends, the length of the flexible shaft sufficient to access a patient's renal artery relative to a percutaneous access location;
a flexible actuation member provided within the lumen and extending between the proximal and distal ends of the shaft, the flexible actuation member moveable within the lumen of the flexible shaft and subject to one or more of elastic deformation, friction, and whip along its length during movement within the flexible shaft's lumen;
a flexible support member coupled to a distal end of the flexible actuation member and extendible beyond a distal tip of the flexible shaft and into a lumen of the renal artery;
an electrode provided at a distal end of the flexible support member and configured to contact an inner wall of the renal artery and deliver high frequency AC energy sufficient to ablate perivascular renal nerve tissue proximate the electrode, the flexible support member configured to urge the electrode into contact with the inner wall of the renal artery; and
a position converter provided at the distal end of the flexible shaft and coupled to the distal end of the flexible actuation member and a proximal end of the flexible support member, the position converter configured to convert movement of the flexible actuation member into at least controlled rotational movement of the flexible support member and the electrode to one of a plurality of stable circumferential positions substantially free of the one or more of elastic deformation, friction, and whip impacting the flexible actuation member movement; wherein the position converter is configured to convert movement of the actuation member into controller axial movement of the flexible support member and the electrode to one of a plurality of stable axial positions.

2. The apparatus of claim 1, wherein:
the position converter is disposed within the lumen of the flexible shaft;
the flexible actuation member and the flexible support member define a continuous member; and
the continuous member is movable within the position converter.

3. The apparatus of claim 1, wherein:
the position converter is disposed within the lumen of the flexible shaft; and
the flexible actuation member and the flexible support member define separate members each having a proximal end and a distal end.

4. The apparatus of claim 1, wherein the position converter comprises a ratcheting arrangement configured to convert axial movement of the flexible actuation member into controlled rotational movement of the flexible support member and the electrode to one of the plurality of stable circumferential positions.

5. The apparatus of claim 1, wherein the position converter comprises a ratcheting arrangement configured to convert axial movement of the flexible actuation member into controlled axial and rotational movement of the flexible support member and the electrode to one of a plurality of stable circumferential and axial positions.

6. The apparatus of claim 4, wherein the ratcheting arrangement comprises a spring-loaded rotating ratcheting element having a proximal end coupled to the distal end of the flexible actuation member and a distal end coupled to the proximal end of the flexible support member, the spring-loaded rotating ratcheting element configured to rotate the flexible support member and the electrode to one of a plurality of stable circumferential positions in response to an actuation force applied to the proximal end of the flexible actuation member.

7. The apparatus of claim 4, wherein the ratcheting arrangement comprises:

a control member having a proximal end, a distal end, and a length extending along the length of the flexible shaft;

a spring-loaded rotating ratcheting element having a proximal end coupled to the distal end of the control member and a distal end coupled to the proximal end of the flexible support member;

a plurality of circumferentially spaced keyways having opposing end locations each of which defines a predetermined stable axial and circumferential position; and a key component provided at a distal end of the flexible support member and having a shape configured to be received by each of the plurality of circumferentially spaced keyways;

wherein the rotating ratcheting element rotatably aligns the key component of the flexible support member with one of the plurality of circumferentially spaced keyways and the aligned flexible support member is axially displaced along said one of the plurality of circumferentially spaced keyways to one of the stable axial and circumferential position in response to each application of an actuation force to the proximal end of the control member.

8. The apparatus of claim 1, wherein the position converter comprises a magnetic indexing arrangement configured to magnetically urge the flexible support member and the electrode to one of the plurality of stable circumferential positions.

9. The apparatus of claim 1, wherein the position converter comprises a magnetic indexing arrangement configured to magnetically urge the flexible support member and the electrode to one of the plurality of stable circumferential positions and one of a plurality of stable axial positions.

10. The apparatus of claim 8, wherein the magnetic indexing arrangement comprises:

a magnet arrangement provided at the distal end of the flexible shaft; and a magnet arrangement provided on the flexible actuation member, the magnet arrangements of the flexible shaft and the flexible actuation member magnetically interacting to urge the flexible support member and the electrode to rotate to one of the plurality of stable circumferential positions in response to an actuation force applied to the proximal end of the flexible actuation member.

11. The apparatus of claim 8, wherein the magnetic indexing arrangement comprises:

a plurality of magnets provided at discrete circumferential and axial locations at the distal end of the shaft; and a plurality of magnets provided on the flexible actuation member at discrete axial locations of the flexible actuation member, the magnets of the flexible shaft and the flexible actuation member magnetically interacting to urge the flexible support member and the electrode to rotate to one of the plurality of stable circumferential positions in response to an actuation force applied to the proximal end of the flexible actuation member.

12. The apparatus of claim 8, wherein the distal end of the flexible shaft comprises a pre-formed spiral shape, and the magnetic indexing arrangement comprises:

a plurality of magnets provided at discrete circumferential and axial locations along the spiral shaped distal end of the flexible shaft; and a plurality of magnets provided on the flexible actuation member at discrete axial locations of the flexible actuation member, the magnets of the flexible shaft and the flexible actuation member magnetically interacting to urge the flexible support member and the electrode to rotate to one of the plurality of stable circumferential positions along the spiral shaped distal end of the flexible shaft in response to an actuation force applied to the proximal end of the flexible actuation member.

13. The apparatus of claim 1, wherein the position converter comprises a geometric keyed orientation mechanism configured to guide a key component of the flexible actuation member into and along a keyway arrangement that limits the movement of the flexible support member and the electrode to one of the plurality of stable circumferential positions.

14. The apparatus of claim 1, wherein the position converter comprises a geometric keyed orientation mechanism configured to guide a key component of the flexible actuation member into and along a keyway arrangement that limits the rotational movement of the flexible support member and the electrode to one of the plurality of stable circumferential positions and limits the axial movement of the flexible support member and the electrode to one of a plurality of stable axial positions.

15. The apparatus of claim 13, wherein the keyway arrangement comprises a plurality of spaced-apart keyways each comprising a tapered entrance configured to guide the key component into alignment with each of the plurality of spaced-apart keyways.

16. The apparatus of claim 13, wherein the keyway arrangement comprises a plurality of circumferentially spaced-apart keyways, with alternate keyways of the keyway arrangement having differing lengths.

17. The apparatus of claim 13, wherein the keyway arrangement comprises a plurality of circumferentially and axially spaced-apart keyways.

18. The apparatus of claim 13, wherein the keyway arrangement comprises a plurality of spaced-apart keyways, the plurality of spaced-apart keyways having one of an elliptical, square, rectangular, and triangular cross-section.

* * * * *